United States Patent
Ohno et al.

(10) Patent No.: US 10,194,811 B2
(45) Date of Patent: Feb. 5, 2019

(54) BLOOD PRESSURE MEASUREMENT DEVICE, BLOOD PRESSURE MEASUREMENT METHOD, AND NON-TRANSITORY RECORDING MEDIUM

(71) Applicant: NEC CORPORATION, Tokyo (JP)

(72) Inventors: Yuji Ohno, Tokyo (JP); Masahiro Kubo, Tokyo (JP); Kimiyasu Takoh, Tokyo (JP); Katsumi Abe, Tokyo (JP); Ersin Altintas, Tokyo (JP); Hiroshi Imai, Tokyo (JP); Osamu Tochikubo, Kanagawa (JP)

(73) Assignee: NEC CORPORATION, Tokyo (JP)

( * ) Notice: Subject to any disclaimer, the term of this patent is extended or adjusted under 35 U.S.C. 154(b) by 28 days.

(21) Appl. No.: 15/118,227

(22) PCT Filed: Feb. 13, 2015

(86) PCT No.: PCT/JP2015/000668
§ 371 (c)(1),
(2) Date: Aug. 11, 2016

(87) PCT Pub. No.: WO2015/122192
PCT Pub. Date: Aug. 20, 2015

(65) Prior Publication Data
US 2017/0181648 A1 Jun. 29, 2017

(30) Foreign Application Priority Data
Feb. 13, 2014 (JP) .................................. 2014-025372

(51) Int. Cl.
*A61B 5/0225* (2006.01)
*A61B 5/022* (2006.01)
(Continued)

(52) U.S. Cl.
CPC ...... *A61B 5/02108* (2013.01); *A61B 5/02225* (2013.01); *A61B 5/6824* (2013.01);
(Continued)

(58) Field of Classification Search
CPC ............ A61B 5/02108; A61B 5/02225; A61B 5/6824; A61B 5/7278; A61B 5/742
(Continued)

(56) References Cited

U.S. PATENT DOCUMENTS 4,850,368 A * 7/1989 Miyawaki .............. A61B 5/022
600/493
4,928,701 A * 5/1990 Harada .............. A61B 5/02116
600/490
(Continued)

FOREIGN PATENT DOCUMENTS

JP 62-38137 A 2/1987
JP 63262125 A 10/1988
(Continued)

OTHER PUBLICATIONS

International Search Report of PCT/JP2015/000668, dated May 12, 2015. [PCT/ISA/210].
(Continued)

*Primary Examiner* — Navin Natnithithadha
(74) *Attorney, Agent, or Firm* — Sughrue Mion, PLLC

(57) ABSTRACT

Disclosed are a blood pressure device, etc., that is capable of highly accurate of blood pressure. The blood pressure device (101) has a blood pressure unit (102) that: finds a specific blood pressure related to pulse wave information (2002), by browsing blood pressure information (2001) associating the pulse wave information and blood pressure related to pulse wave signals caused by blood pressure during a specific period and measured, the pulse wave information associating blood pressure during the specific period and the pulse
(Continued)

wave signals; and estimates the blood pressure relating to the pulse wave information (2002) on the basis of the found specific blood pressure.

8 Claims, 26 Drawing Sheets

(51) Int. Cl.
*A61B 5/021* (2006.01)
*A61B 5/00* (2006.01)

(52) U.S. Cl.
CPC .......... *A61B 5/7207* (2013.01); *A61B 5/7278* (2013.01); *A61B 5/742* (2013.01); *A61B 5/0225* (2013.01)

(58) Field of Classification Search
USPC .................. 600/481, 483–485, 500–503
See application file for complete search history.

(56) References Cited

U.S. PATENT DOCUMENTS

| | | | |
|---|---|---|---|
| 5,261,414 A * | 11/1993 | Aung | A61B 5/02116 600/496 |
| 5,279,303 A * | 1/1994 | Kawamura | A61B 5/0225 600/496 |
| 5,551,438 A * | 9/1996 | Moses | A61B 5/02225 600/485 |
| 5,649,536 A | 7/1997 | Ogura et al. | |
| 5,791,348 A * | 8/1998 | Aung | A61B 5/02116 600/493 |
| 5,836,888 A | 11/1998 | Ogura et al. | |
| 5,931,790 A * | 8/1999 | Peel, III | A61B 5/02225 600/494 |
| 6,045,510 A | 4/2000 | Ogura et al. | |
| 6,241,680 B1 * | 6/2001 | Miwa | A61B 5/02255 600/490 |
| 6,251,081 B1 * | 6/2001 | Narimatsu | A61B 5/02125 600/485 |
| 6,338,718 B1 * | 1/2002 | Ogura | A61B 5/022 600/485 |
| 6,346,083 B1 * | 2/2002 | Nishibayashi | A61B 5/02116 600/485 |
| 6,355,000 B1 * | 3/2002 | Ogura | A61B 5/022 600/490 |
| 6,379,309 B1 * | 4/2002 | Ogura | A61B 5/022 600/485 |
| 6,413,224 B1 | 7/2002 | Ogura et al. | |
| 6,497,668 B2 * | 12/2002 | Nishibayashi | A61B 5/02116 600/494 |
| 6,517,493 B2 * | 2/2003 | Ogura | A61B 5/022 600/485 |
| 6,561,985 B2 * | 5/2003 | Ito | A61B 5/0225 600/494 |
| 6,565,515 B2 * | 5/2003 | Ogura | A61B 5/0225 600/490 |
| 6,592,528 B2 * | 7/2003 | Amano | A61B 5/02007 600/485 |
| 6,802,814 B2 * | 10/2004 | Narimatsu | A61B 5/02116 600/485 |
| 6,913,575 B2 * | 7/2005 | Nishibayashi | A61B 5/022 600/485 |
| 6,929,610 B2 * | 8/2005 | Forstner | A61B 5/022 600/485 |
| 7,232,412 B2 * | 6/2007 | Shirasaki | A61B 5/02116 600/490 |
| 7,361,148 B2 * | 4/2008 | Narimatsu | A61B 5/022 600/490 |
| 8,398,556 B2 * | 3/2013 | Sethi | A61B 5/021 600/485 |
| 2002/0002340 A1 * | 1/2002 | Nishibayashi | A61B 5/02116 600/494 |
| 2002/0120199 A1 | 8/2002 | Ogura et al. | |
| 2004/0147848 A1 * | 7/2004 | Shirasaki | A61B 5/02116 600/490 |
| 2005/0119578 A1 * | 6/2005 | Kubo | A61B 5/02116 600/490 |
| 2017/0172429 A1 * | 6/2017 | Takoh | A61B 5/7207 |

FOREIGN PATENT DOCUMENTS

| | | |
|---|---|---|
| JP | 7-236616 A | 9/1995 |
| JP | 07275214 A | 10/1995 |
| JP | 11-47103 A | 2/1999 |
| JP | 2000083911 A | 3/2000 |
| JP | 2002272690 A | 9/2002 |
| JP | 2003-250770 A | 9/2003 |
| JP | 2003-284696 A | 10/2003 |
| JP | 2005-66087 A | 3/2005 |
| JP | 2005-261505 A | 9/2005 |
| JP | 2005-288002 A | 10/2005 |
| JP | 2010-194111 A | 9/2010 |
| JP | 2012071059 A | 4/2012 |

OTHER PUBLICATIONS

Written Opinion of PCT/JP2015/000668, dated May 12, 2015. [PCT/ISA/237].

Communication dated May 15, 2018 from the Japanese Office Action in counterpart Japanese application No. 2014-214001.

* cited by examiner

BLOOD PRESSURE INFORMATION

PULSE WAVE INFORMATION

| PRESSURE SIGNAL | PULSE WAVE SIGNAL | PULSE WAVE SIGNAL |
|---|---|---|
| ... | ... | ... |
| 70 | aa | ba |
| 72 | ab | bb |
| 74 | ac | bc |
| ... | ... | ... |
| 120 | ax | bx |
| 122 | ay | by |
| 124 | az | bz |
| ... | ... | ... |

| DIASTOLIC BLOOD PRESSURE | SYSTOLIC BLOOD PRESSURE |
|---|---|
| ○△□ | ×□○ |

BLOOD PRESSURE

Fig. 7

| PRESSURE SIGNAL | PULSE WAVE SIGNAL A | PULSE WAVE SIGNAL B |
|---|---|---|
| ... | ... | ... |
| 70 | aa | ba |
| 72 | ab | bb |
| 74 | ac | bc |
| ... | ... | ... |
| 120 | ax | bx |
| 122 | ay | by |
| 124 | az | bz |
| ... | ... | ... |

BLOOD PRESSURE MEASUREMENT DEVICE, BLOOD PRESSURE MEASUREMENT METHOD, AND NON-TRANSITORY RECORDING MEDIUM

CROSS REFERENCE TO RELATED APPLICATIONS

This application is a National Stage of International Application No. PCT/JP2015/000668 filed Feb. 13, 2015, claiming priority based on Japanese Patent Application No. 2014-025372, filed Feb. 13, 2014, the contents of all of which are incorporated herein by reference in their entirety.

TECHNICAL FIELD

The present invention relates to a blood pressure estimation device and the like that estimate a blood pressure.

BACKGROUND ART

A blood pressure is one index for analyzing the presence or absence of a cardiovascular disease. For example, analysis based on a blood pressure of a risk such as a so-called lifestyle-related disease is effective for preventing diseases in the cardiovascular system such as stroke, heart failure, and heart attack. Specifically, at outside of the hospital such as at home, it is desirable to measure a blood pressure over a long period at the same time every day in a fixed (or substantially fixed) environment. A blood pressure measured outside of the hospital is suitable for predicting diseases in the cardiovascular system with a high degree of accuracy. Therefore, a blood pressure measured outside of the hospital such as at home tends to be emphasized in medical practice. Further, it is also very important for curing hypertension to accurately measure a blood pressure.

A blood pressure fluctuates depending on a living activity pattern in a time period such as one year, one month, or 24 hours. Further, the blood pressure greatly fluctuates depending on various factors such as an activity amount, conversation, psychological anxiety, tension, impatience, astonishment, patience, alcohol-intake, smoking, and coldness other than pathological factors.

Research has also been conducted in recent years for estimating a risk of occurrence of a disorder in an organ on the basis of a difference among a blood pressure measured while sleeping, a blood pressure measured while being active, and a blood pressure measured when waking up in the morning.

For example, a blood pressure meter (ABPM) disclosed by PTL 1 and PTL 2 is a blood pressure meter that regularly measures a blood pressure by being carried by a person to be measured for 24 hours in order to measure a blood pressure in various situations. ABPM is an abbreviation for Ambulatory_Blood_Pressure_Monitoring. According to "Guidelines for Usage (ABPM) Standards of Blood Pressure Meters Carried for 24 Hours," a measurement interval is a time interval ranging from 10 to 30 minutes. Further, according to the guidelines, it is necessary for a person to be measured to record daily activities (e.g. bedtime, wake-up time, sleep depth, meals, excretions, dosing, and the like).

PTL 3 to PTL 5 disclose common blood pressure meters (blood pressure measurement devices).

PTL 3 discloses a Non Invasive blood pressure measurement device in which the noise can be eliminated and which has a small burden on a person to be measured. The blood pressure measurement device includes a function for eliminating noise from a measured pulse wave.

The blood pressure measurement device disclosed in PTL 4 measures pulse waves with a plurality of pulse wave sensors and calculates a starting time of a pulse wave having a largest amplitude of the measured pulse waves. The blood pressure measurement device calculates an internal pressure of a cuff at the calculated point of time as a maximum blood pressure.

The electronic blood pressure meter disclosed in PTL 5 includes an oscillometric measurement unit for measuring a blood pressure on the basis of a pulse wave and a calculation unit for calculating a waveform parameter representing a waveform corresponding to a relative pressure of the pulse wave to an internal pressure of a cuff. The electronic blood pressure meter further includes an update unit for calibrating the calculated blood pressure on the basis of the calculated waveform parameter.

CITATION LIST

Patent Literature

PTL 1: Japanese Laid-open Patent Publication No. 11(1999)-47103

PTL 2: Japanese Laid-open Patent Publication No. 2010-194111

PTL 3: Japanese Laid-open Patent Publication No. 2005-288002

PTL 4: Japanese Laid-open Patent Publication No. S62 (1987)-038137

PTL 5: Japanese Laid-open Patent Publication No. 2003-250770

SUMMARY OF INVENTION

Technical Problem

A blood pressure measurement device (blood pressure meter), for example an ABPM device, sets an internal pressure of a cuff to be higher than a blood pressure (a systolic blood pressure value, a maximum blood pressure, or a Systolic_blood_pressure, expressed also as an "SBP") in a course of heart contraction. Therefore, the blood pressure measurement device may become a significant burden on a person to be measured. Therefore, pressurization upon measurement of a blood pressure is controlled and a systolic blood pressure is estimated in order to reduce the burden on the person to be measured.

PTL 2 discloses a Non_Invasive blood pressure measurement device and a blood pressure measurement program that control a pressure in a cuff and thereby reduce a burden on a person to be measured.

The blood pressure measurement device disclosed by PTL 2 measures a correct blood pressure only in a quiet environment or a particular situation. For this reason, it is difficult for the blood pressure measurement device to accurately measure a blood pressure when, for example, a person to be measured is exercising or a person to be measured stays in a place surrounded by large noise. Therefore, the blood pressure measurement device is unsuitable for applications such as ABPM.

On the other hand, according to the guidelines for ABPM standards, when a blood pressure measurement is started while walking or engaging in manual labor, it is necessary for a person to be measured to keep an upper arm where a blood pressure is measured rested. However, the person to be measured is not always in a state of rest, and therefore, it is desired for a blood pressure to be measured without being in a state of rest.

Accordingly, a main object of the present invention is to provide a blood pressure measurement device and the like that accurately measure a blood pressure.

Solution To Problem

As an aspect of the present invention, a blood pressure estimation device including:

blood pressure estimation means for determining a particular blood pressure associated with particular pulse wave information by referring to blood pressure information where (i) pulse wave information where a pressure in a certain time period and a pulse wave signal measured on the basis of the pressure in the certain time period are associated and (ii) a blood pressure for the pulse wave signal are associated, and estimating a blood pressure for the particular pulse wave information on the basis of the determined particular blood pressure.

In addition, as another aspect of the present invention, a blood pressure estimation method including:

determining, by using an information processing device, a particular blood pressure associated with particular pulse wave information by referring to blood pressure information where (i) pulse wave information where a pressure in a certain time period and a pulse wave signal measured on the basis of the pressure in the certain time period are associated and (ii) a blood pressure for the pulse wave signal are associated, and estimating a blood pressure for the particular pulse wave information on the basis of the determined particular blood pressure.

Furthermore, the object is also realized by a blood pressure estimation program, and a computer-readable recording medium which records the program.

Advantageous Effects of Invention

According to the blood pressure estimation device and the like of the present invention, a blood pressure can be estimated with a high degree of accuracy.

BRIEF DESCRIPTION OF DRAWINGS

FIG. 4 is a diagram conceptually illustrating blood pressure information as one example of blood pressure information.

FIG. 7 is a diagram conceptually illustrating one example of pulse wave information.

FIG. 9 is a perspective view of a vicinity of a cuff that is not put on.

DESCRIPTION OF EMBODIMENTS

Next, exemplary embodiments of the present invention will be described in detail with reference to the drawings.

<First Exemplary Embodiment>

Figure 1:
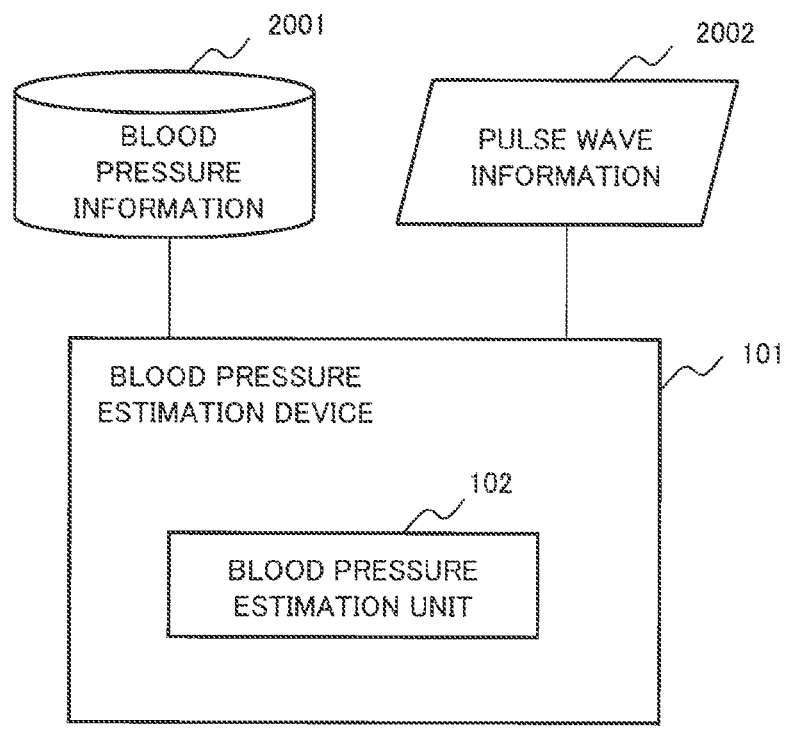
FIG. 1 is a block diagram illustrating components included in a blood pressure estimation device according to a first exemplary embodiment of the present invention.
Figure 2:
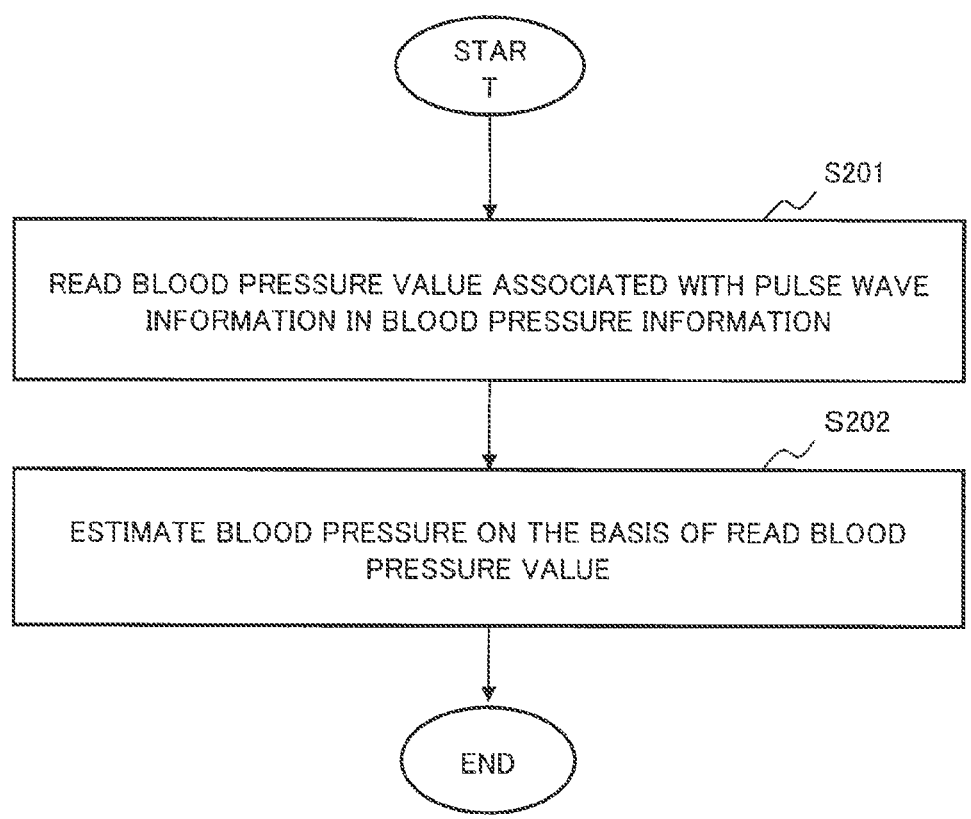
FIG. 2 is a flowchart illustrating a flow of processing in the blood pressure estimation device according to the first exemplary embodiment.

Components included in a blood pressure estimation device 101 according to a first exemplary embodiment of the present invention and processing executed by the blood pressure estimation device 101 will be described in detail with reference to FIG. 1 and FIG. 2. FIG. 1 is a block diagram illustrating the components included in the blood pressure estimation device 101 according to the first exemplary embodiment of the present invention. FIG. 2 is a flowchart illustrating a flow of processing in the blood pressure estimation device 101 according to the first exemplary embodiment.

The blood pressure estimation device 101 according to the first exemplary embodiment includes a blood pressure estimation unit 102.

The blood pressure estimation device 101 receives pulse wave information 2002 in which a pressure signal in a certain time period and multiple pulse wave signals measured when a pressure indicated by the pressure signal in the certain time period is applied to a person to be measured are associated with each other.

Hereinafter, for convenience of description, with respect to the multiple pulse wave signals, it is assumed that there are two pulse wave signals. The pulse wave information 2002 according to the present exemplary embodiment may include three or more pulse wave signals as described later.

Figure 5:
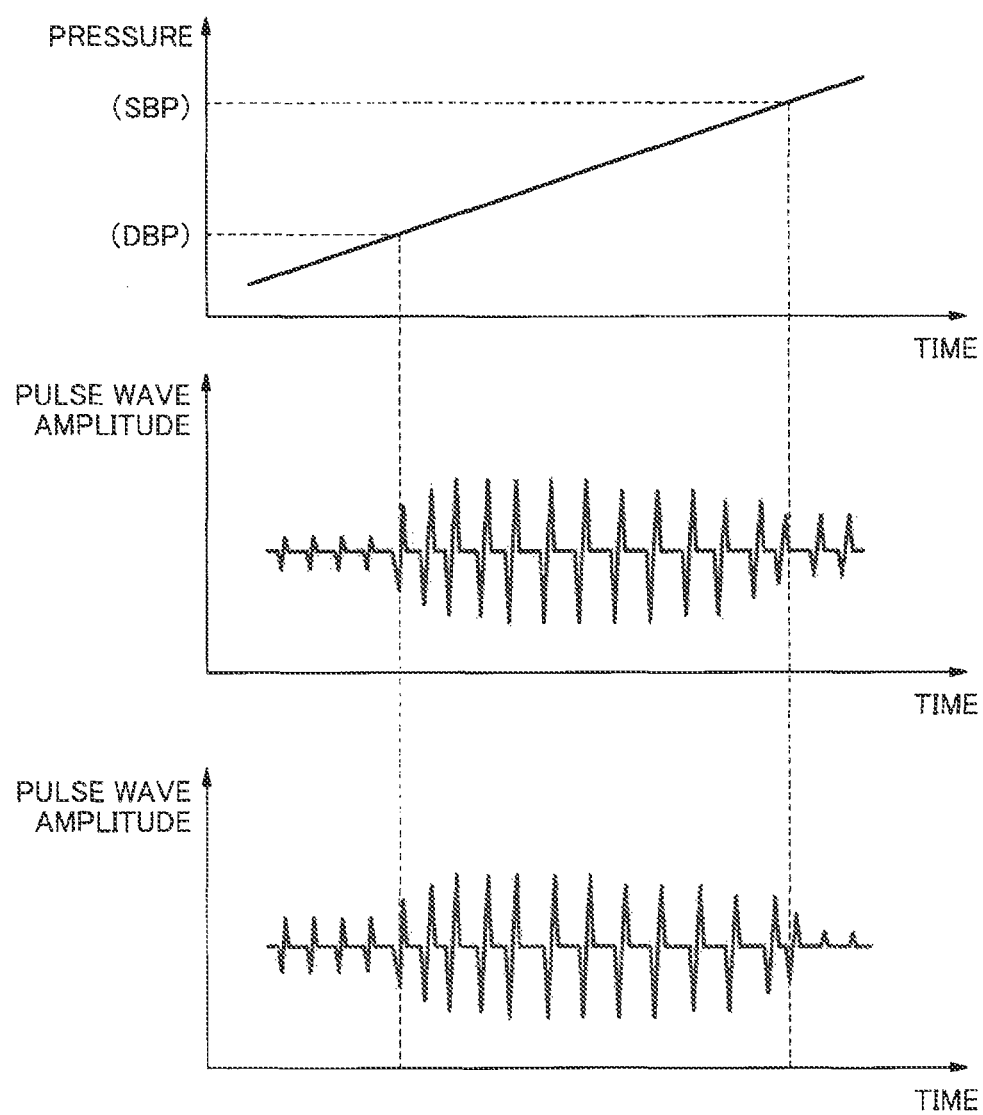
FIG. 5 is a diagram conceptually illustrating one example of a pressure signal and pulse wave signals.

With reference to FIG. 5, the multiple pulse wave signals and the pressure signal in the pulse wave information 2002 will be described. FIG. 5 is a diagram conceptually illustrating one example of the pressure signal and the multiple pulse wave signals. The horizontal axis of FIG. 5 represents time, and represents a later time at a rightward position. The vertical axis in the upper figure of FIG. 5 represents an amplitude of a pressure signal and represents that the pressure signal is stronger toward the upper side. The vertical axis in the middle figure of FIG. 5 and the lower figure of FIG. 5 represents an amplitude of a pulse wave signal and represents that the amplitude of the pulse wave signal increases as being closer to the upper end or the lower end, and the amplitude of the pulse wave signal decreases as being closer to a center of the upper end and the lower end. In the example illustrated in FIG. 5, the certain time period refers to a (heartbeat) period in which the heart beats at multiple times. The figure illustrated in the upper part of FIG. 5 illustrates one example of the pressure signal, and the two figures illustrated in the lower part of FIG. 5 illustrate one example of the pulse wave signal.

Figure 6:
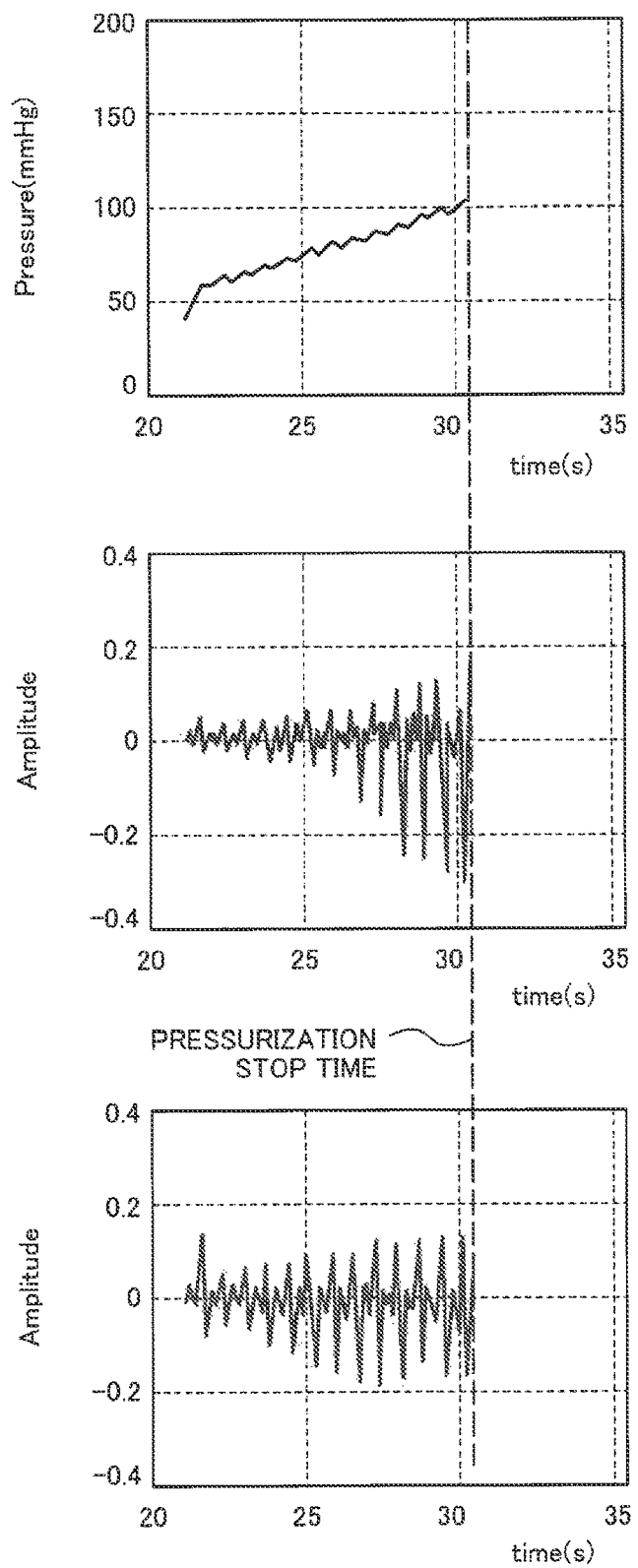
FIG. 6 is a diagram conceptually illustrating one example of a pressure signal and pulse wave signals.

Further, the pulse wave information may be pulse wave information in a certain period, for example, as illustrated in FIG. 6. FIG. 6 is a diagram conceptually illustrating one example of a pressure signal and a pulse wave signal. The pulse wave information illustrated in FIG. 6 is information on a pulse wave signal measured when pressurization is stopped at a pressure (approximately 100 mmHg in this case) lower than a systolic blood pressure. The figure in the upper part of FIG. 6 illustrates one example of the pressure signal, and the two figures illustrated in the lower part of FIG. 6 illustrate one example of the pulse wave signal.

When in a certain time period, a pressure lies somewhere between a systolic blood pressure and a diastolic blood pressure measured in the course of heart contraction (a diastolic blood pressure value, a minimum blood pressure, or a Diastolic blood pressure, hereinafter, expressed also as a "DBP"), an amplitude in a pulse wave is large and a pulse wave for a person to be measured can be detected. On the contrary, when the pressure has a value larger than the systolic blood pressure or a value smaller than the diastolic blood pressure, an amplitude in the pulse wave specifically in a downstream is small, and therefore, it is difficult to detect a pulse wave for the person to be measured.

The pulse wave information is information where a pressure signal at a certain timing is associated with multiple pulse wave signals, as illustrated in FIG. 7. FIG. 7 is a diagram conceptually illustrating one example of the pulse wave information. In the pulse wave information, for example, a pressure signal "70," a pulse wave signal A "aa," and a pulse wave signal B "ba" are associated with each other. This represents that the pulse wave signal A "aa" and the pulse wave signal B "ba" are measured when a pressure "70" is applied to a person to be measured.

In the pulse wave information, a pressure signal at a certain timing need not always be associated with multiple pulse wave signals, and may be a value of parameters calculated by regression analysis and the like of a relation between the pressure signal and the multiple pulse wave signals. Further, the pulse wave information may not be multiple pulse wave signals themselves or a pressure signal itself, and may be a value calculated on the basis of the pressure signal or on the basis of the multiple pulse wave signals in accordance with predetermined steps. In other words, the pulse wave information is not limited to the above-described examples.

Figure 3:
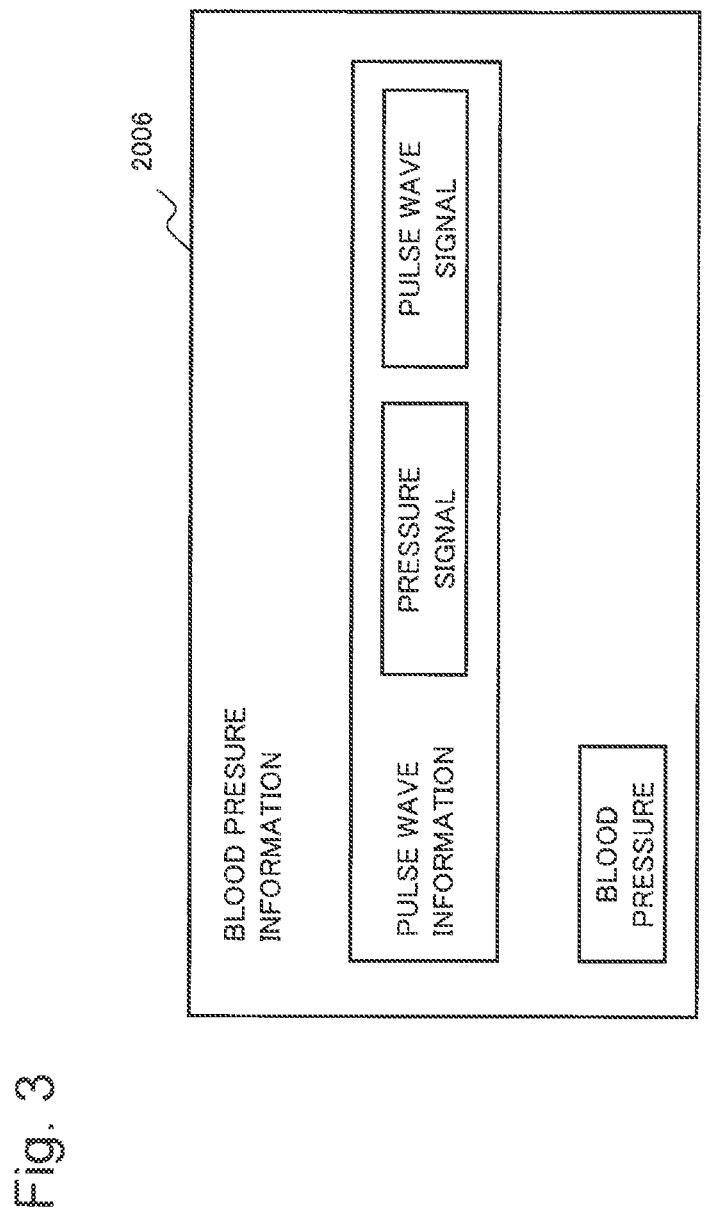
FIG. 3 is a diagram conceptually illustrating components included in blood pressure information.

The blood pressure estimation device 101 can refer to blood pressure information 2001 (e.g. blood pressure information 2006 as illustrated in FIG. 3) in which pulse wave information and a blood pressure are associated with each other. FIG. 3 is a diagram conceptually illustrating components included in the blood pressure information 2006. In the blood pressure information 2006 pulse wave information are associated with a blood pressure, as described above.

With reference to FIG. 4, one example of the blood pressure information 2001 will be described. FIG. 4 is a diagram conceptually illustrating blood pressure information 2007 as one example of the blood pressure information 2001. In this case, a blood pressure includes a diastolic blood pressure and a systolic blood pressure. Further, in the example illustrated in FIG. 4, in pulse wave information, a pressure signal is associated with multiple pulse wave signals.

The blood pressure estimation unit 102 reads a blood pressure associated with the received pulse wave information 2002 from the blood pressure information 2001 (step S201). In other words, the blood pressure estimation unit 102 refers to the blood pressure information 2001 and thereby determines a blood pressure associated with the received pulse wave information 2002.

In the above-described example, the blood pressure estimation unit 102 searches pulse wave information coincident with the pulse wave information 2002 in the blood pressure information 2001. However, the blood pressure estimation unit 102, for example, may calculate a degree of similarity (or a degree of correlation) representing an extent that the pulse wave information 2002 and pulse wave information in the blood pressure information 2001 are similar to each other and search similar (or coincident) pulse wave information on the basis of the calculated degree. Further, there may be a plurality of pieces of blood pressure information. Alternatively, the blood pressure estimation unit 102 may select pulse wave information having a highest (or approximately highest) degree of similarity and read a blood pressure associated with the selected pulse wave information.

For example, "the approximately highest" can be defined as a value that falls within a certain range from a maximum. The certain range may be a predetermined value.

Further, it is not always necessary for the blood pressure estimation unit 102 to calculate degrees of similarity between all pieces of data of pulse wave information in the blood pressure information 2001 and the pulse wave information 2002. The blood pressure estimation unit 102 may calculate degrees of similarity on the basis of a part of the pieces of date of the pulse wave information in the blood pressure information 2001. In other words, in this case, it is not always necessary for a pressure in the pulse wave information to include a diastolic blood pressure and a systolic blood pressure.

Then, the pressure estimation device 101 estimates a blood pressure (hereinafter, expressed as a "first blood pressure" for convenience of description) for the pulse wave information 2002 on the basis of the read blood pressure (step S202). When, for example, there is one read blood pressure, the blood pressure estimation unit 102 may estimate the read blood pressure as the first blood pressure. Further, when estimating a blood pressure read in accordance with a degree of similarity or a degree of correlation, the blood pressure estimation unit 102 may estimate the first blood pressure by determining a weighted average value and the like in accordance with a degree of similarity for the read blood pressure.

The blood pressure information 2001 includes pulse wave information where a pressure signal with multiple pulse wave signals previously measured and a blood pressure about a person to be measured are associated with each other. The blood pressure information (information of a pressure signal, multiple pulse wave signals, and a blood pressure) 2001 may be prepared before a blood pressure estimation is started. In a method for previously measuring blood pressure information, in manner similar that in the present exemplary embodiment, pulse wave information (a pressure signal and multiple pulse wave signals) is acquired, a blood pressure (a systolic blood pressure and a diastolic blood pressure) is measured in accordance with an oscillometric method or a Korotkoff method, and the measured blood pressure and the acquired pulse wave information are associated with each other. As another method, in a manner similar to that in the present exemplary embodiment, it is possible to acquire pulse wave information, calculate a blood pressure on the basis of a characteristic of the pulse wave information, and associate the calculated blood pressure with the acquired pulse wave information to generate blood pressure information. The method for previously measuring blood pressure information is not limited to the above-described methods. In this case, there may be a plurality of persons to be measured.

Further, the pulse wave information 2002 need not be a table form as exemplified in FIG. 7. The pulse wave information 2002 may be, for example, a relation equation representing a relation (e.g. FIG. 5 and FIG. 6) between a pressure and multiple pulse wave signals or a parameter representing the relation equation.

A large degree of similarity represents, for example, a small difference between a value included in the blood pressure information 2001 and a value included in the pulse wave information 2002. A large degree of correlation represents, for example, a large correlation coefficient between a value included in the blood pressure information 2001 and the pulse wave information 2002. The degree of similarity and the degree of correlation are not limited to the above-described examples.

The blood pressure estimation device 101 according to the present exemplary embodiment selects a blood pressure associated with the pulse wave information 2002 where a blood pressure signal is associated with multiple pulse wave signals from the blood pressure information 2001, and estimates a blood pressure for the pulse wave information 2002 on the basis of the read blood pressure. Therefore, even when a pulse wave or a pressure value includes noise, the blood pressure estimation device 101 reads a blood pressure from pulse wave information including multiple pulse wave signals and blood pressure information and can thereby estimate a blood pressure with reducing an influence of the noise.

On the other hand, it is difficult for a common blood pressure estimation device to accurately measure a blood pressure when a measured pulse includes noise, as described above.

In other words, according to the blood pressure estimation device 101 of the present exemplary embodiment, a blood pressure can be estimated with a high degree of accuracy.

Figure 8:
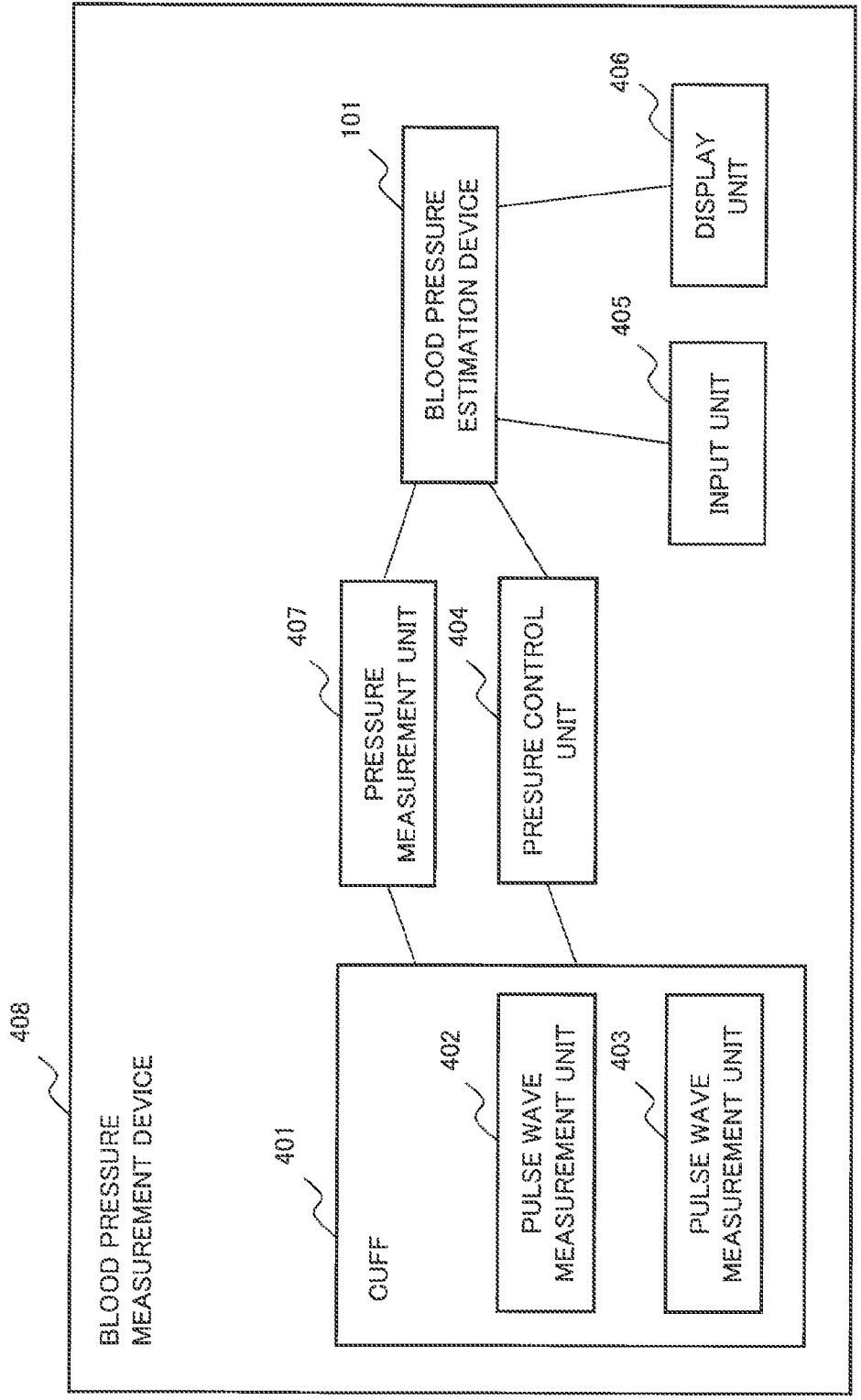
FIG. 8 is a block diagram illustrating components included in a blood pressure measurement device according to the first exemplary embodiment.

The blood pressure estimation device 101 receives, for example, pulse wave information where a pressure signal measured by a blood pressure measurement device 408 exemplified in FIG. 8 is associated with multiple pulse wave signals measured by the blood pressure measurement device 408. FIG. 8 is a block diagram illustrating components included in the blood pressure measurement device 408 according to the first exemplary embodiment.

Figure 9:
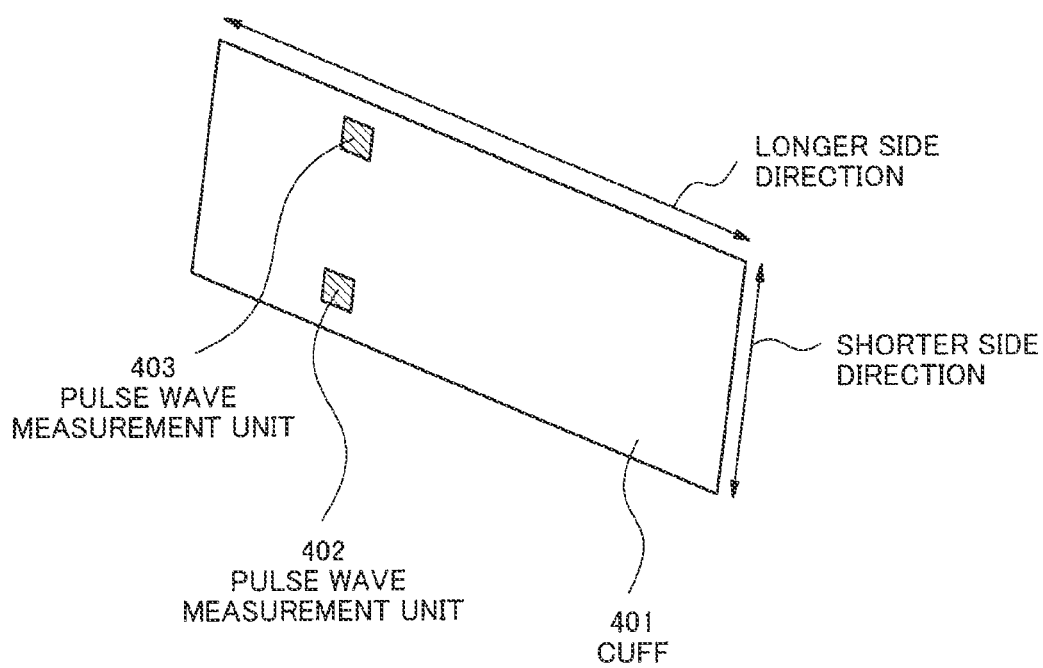

The blood pressure measurement device 408 includes a cuff 401, a pulse wave measurement unit 402, a pulse wave measurement unit 403, a pressure measurement unit 407, a pressure control unit 404, an input unit 405, a display unit 406, and the blood pressure estimation device 101. As exemplified in FIG. 9, the cuff 401, the pulse wave measurement unit 402, and the pulse wave measurement unit 403 are integrally formed. FIG. 9 is a perspective view of a vicinity of the cuff 401 that is not put on.

In the following description, for convenience of description, it is assumed that a shape of the cuff 401 is a rectangle (rectangular shape), a trapezoid, or a shape close to a rectangular shape while being developed as exemplified in FIG. 9. The shape close to a rectangular shape is, for example, a shape formed in a tapered or arced manner in a shorter side direction, a longer side direction, or both directions. The shape close to a rectangular shape is not limited to the above-described shape. It is assumed that the longer side direction is a direction where the cuff is wound around a specific region, i.e. a circumference direction while being wound around the specific region. Further, it is assumed that the shorter side direction is a direction orthogonal (or substantially orthogonal) to the longer side direction. Further, it is assumed that the entire cuff applies a pressure to the specific region in a state of pressurization. In this case, it is assumed that an "upstream" represents a portion between the nerve center or the heart and the center of the shorter side direction in an artery. It is assumed that a "downstream" represents a portion between the center of the shorter side direction and a peripheral side (e.g. a hand or foot) in the artery. However, an aspect of the cuff is not limited to the above-described manner.

Figure 10:
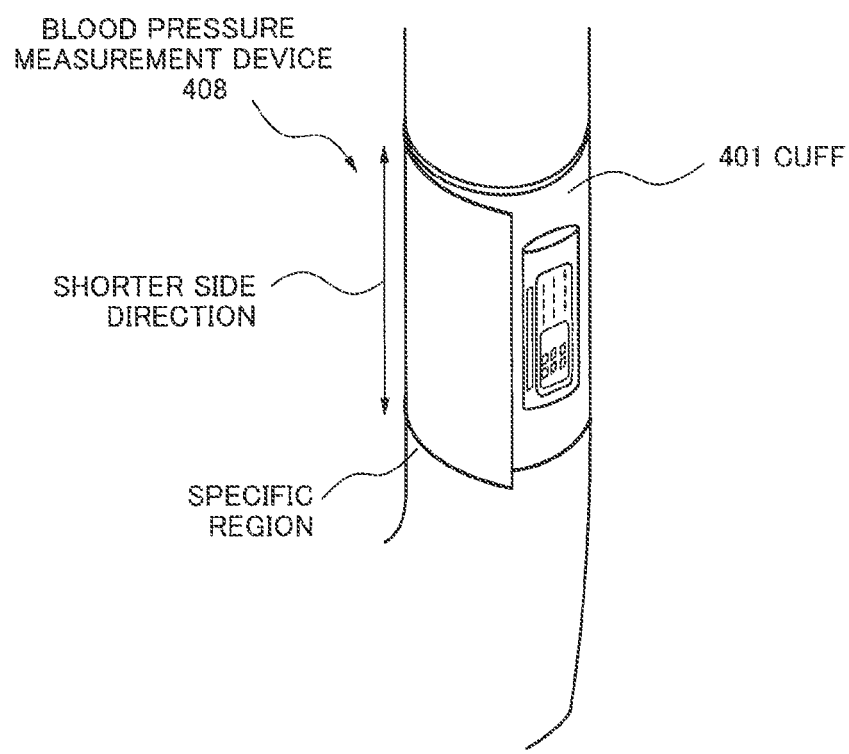
FIG. 10 is a diagram illustrating one example of a state where a cuff is put on a specific region.

First, as shown in FIG. 10, a person to be measured winds the cuff 401 around a specific region such as an upper arm, a leg, a wrist, or the like and measures a blood pressure. The person to be measured winds the longer side direction around the specific region to place the cuff 401. FIG. 10 is a diagram illustrating one example of a state where the cuff 401 is put on a specific region. In this case, it is conceivable that an artery is parallel (or substantially parallel) to the shorter side direction. In this case, the pulse wave measurement unit 402 measures a pulse wave in a portion between the nerve center or the heart and the center of the shorter side direction. On the other hand, the pulse wave measurement unit 403 measures a pulse wave in a portion between the center of the shorter side direction and a peripheral side (e.g. a hand or foot).

The pulse wave measurement unit 402 and the pulse wave measurement unit 403 each are, for example, a vibration sensor that detects vibrations caused by a pulse wave or a photoelectric sensor that detects reflected light when a specific region is irradiated with light or transmitted light when a specific region is irradiated with light. The pulse wave measurement unit 402 and the pulse wave measurement unit 403 may be sensors different from each other. It is possible that the pulse wave measurement unit 402 is a photoelectric sensor for a first wavelength (e.g. red light of approximately 660 nm) and the pulse wave measurement unit 403 is a photoelectric sensor for a second wavelength (e.g. near-infrared light of approximately 940 nm) different from the first wavelength. Herein, "nm" represents nanometers.

Further, the pulse wave measurement unit 402 and the pulse wave measurement unit 403 may be a pressure sensor. In the case of the pressure sensor, the pulse wave measurement unit decomposes a pressure signal into signals having cycles different from each other, for example, via Fourier transformation or the like. When the pressure control unit 404 performs pressurization or depressurization at a constant (or substantially a constant) speed, a cycle for a pressure resulting from the pressure control unit 404 takes a long time. Therefore, when a signal having a short cycle is extracted from the pressure signal via a combination with a filter circuit or the like or an application of a digital filter, the pulse wave measurement unit can extract a pulse wave signal resulting from a pulse wave. The pulse wave measurement unit is not limited to the above-described examples. As the pulse wave measurement unit, for example, a magnetic sensor, an acceleration sensor or the like is applicable.

The person to be measured operates the input unit 405 to start a measurement. The input unit 405 includes, for example, a measurement start button for starting a measurement, a power button, a measurement stop button for cancelling the measurement after the measurement start, and a left button and a right button used upon selecting an item displayed by the display unit 406 (each thereof being not illustrated). The input unit 405 transmits an input signal received from a person to be measured or the like to the blood pressure estimation device 101.

In response to the measurement start, the pressure control unit 404 controls an amount of gas (e.g. air), liquid, or both sealed in the cuff 401 while referring to an internal pressure of the cuff 401 measured by the pressure measurement unit 407 to control a pressure applied to a specific region. The pressure control unit 404 controls, for example, operations of a pump that sends the gas sealed in the cuff 401 or a valve in the cuff 401.

The cuff 401 may include a pressure bag (air bag) in which air is sealed or a pressure bag 1006 (e.g. FIG. 11A to be described later) such as a gel bag in which gel or liquid is sealed. The cuff 401 applies a pressure to the specific region in accordance with control executed by the pressure control unit 404.

Figure 11A:
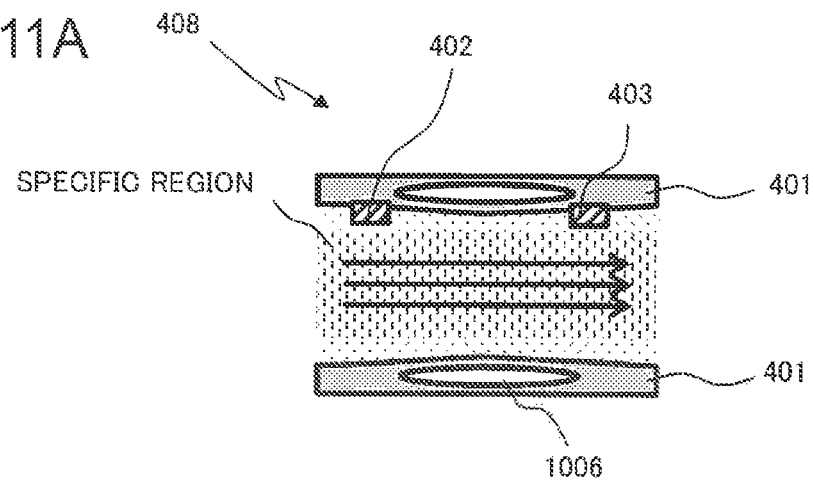
FIG. 11A is a diagram conceptually illustrating one example of a position relation between a cuff and pulse wave measurement units.

The pulse wave measurement unit 402 and the pulse wave measurement unit 403 may be disposed to sandwich a pressurization center (or substantially the center) of the shorter side direction of the cuff 401. FIG. 11A is a diagram conceptually illustrating one example of a position relation between a cuff and pulse wave measurement units. An optimum disposition of pulse wave sensors refers to a case in which the pulse wave measurement unit 402 and the pulse wave measurement unit 403 are located at each end of the pressure bag 1006. In other words, this disposition is a configuration that is located on a pressure unit in which a pulse wave is easily acquired and is large in a difference. For convenience of description, FIG. 11A also illustrates a specific region and a blood flow in the specific region. However, the blood pressure measurement device 408 does not include a specific region or a blood flow in the specific region.

Figure 11B:
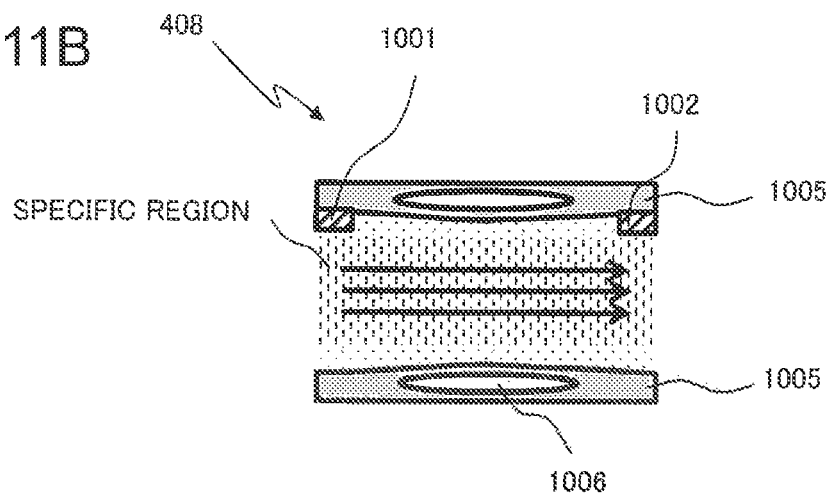
FIG. 11B is a diagram conceptually illustrating one example of a position relation between a cuff and pulse wave measurement units.

FIG. 11B is a diagram conceptually illustrating one example of a position relation between a cuff and pulse wave measurement units, different from FIG. 11A. A configuration illustrated in FIG. 11B is a configuration in which a pulse wave measurement unit 1001 and a pulse wave measurement unit 1002 are disposed at each end of the cuff so that a difference between pulse wave signals measured by the pulse wave measurement unit 1001 and the pulse wave measurement unit 1002 is largest. For convenience of description, FIG. 11B also illustrates a specific region and a blood flow in the specific region. However, the blood pressure measurement device 408 does not include a specific region or a blood flow in the specific region.

Figure 11C:
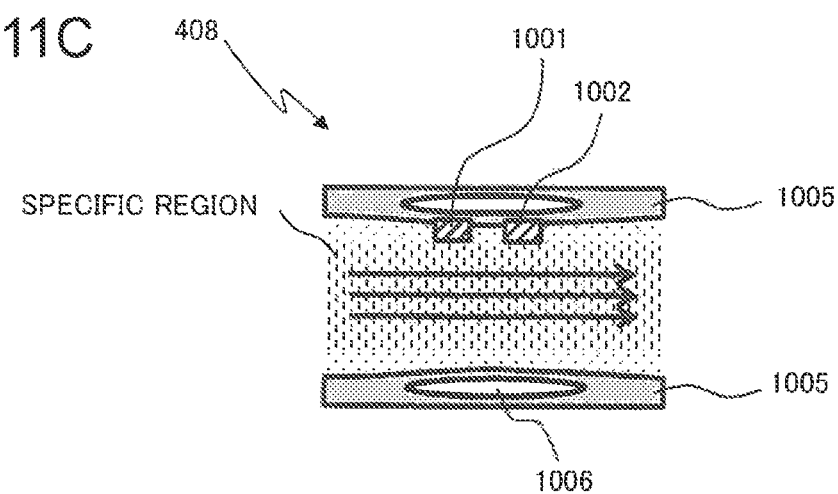
FIG. 11C is a diagram conceptually illustrating one example of a position relation between a cuff and pulse wave measurement units.

FIG. 11C is a diagram conceptually illustrating one example of a position relation between a cuff and pulse wave measurement units. A configuration illustrated in FIG. 11C is a configuration in which the pulse wave measurement unit 1001 and the pulse wave measurement unit 1002 are disposed at a center (or substantially a center) of a pressure unit. In the case of the configuration, the pulse wave measurement unit 1001 and the pulse wave measurement unit 1002 easily measure pulse wave signals. For convenience of description, FIG. 11C also illustrates a specific region and a blood flow in the specific region. However, the blood pressure measurement device 408 does not include a specific region or a blood flow in the specific region.

The position relation between the cuff and the pulse wave measurement units is not limited to the above-described examples and may be a configuration in which easiness in measurement of pulse wave signals or a difference is considered. The pulse wave measurement units easily measure pulse waves as being closer to a center (or substantially a center) of the pressure unit and easily measure a difference as being distant from the center (or substantially the center) of the pressure unit (i.e. as being closer to each cuff end). The configuration may be, for example, a configuration in which the pulse wave measurement unit 402 is disposed at an end of the pressure unit and the pulse wave measurement unit 403 is disposed at an end of the cuff or a configuration in which the pulse wave measurement unit 402 is disposed at an end of the cuff and the pulse wave measurement unit 403 is disposed in a vicinity of the center of the pressure unit. In addition, the configuration may be a configuration in which the pulse wave measurement unit 402 is disposed at an end of the cuff and the pulse wave measurement 403 is disposed at an end of the pressure unit or the pulse wave measurement unit 402 is disposed at the end of the cuff and the pulse wave measurement unit 403 is disposed in a vicinity of the center of the pressure unit. Further, the configuration may be a configuration in which the pulse wave measurement unit 402 is disposed in a vicinity of the center of the pressure unit and the pulse wave measurement unit 403 is disposed at an end of the pressure unit or a configuration in which the pulse wave measurement unit 402 is disposed in a vicinity of the center of the pressure unit and the pulse wave measurement unit 403 is disposed at an end of the cuff.

For example, the pressure measurement unit 407 discretizes a measured pressure, causes the discretized pressure to be subjected to conversion (analog digital conversion, or A/D conversion) into a digital signal, and transmits the digital signal as a pressure signal. Similarly, for example, the pulse wave measurement unit 402 and the pulse wave measurement unit 403 each discretize a measured pulse wave, converts the discretized pulse wave to a digital signal, and transmits the digital signal as a pulse wave signal.

Upon A/D conversion, a filter or the like that extracts a particular frequency may be used to extract a part of a pressure (or a pulse wave). Further, the pressure (or the pulse wave) may be amplified to a predetermined amplitude by applying an amplifier or the like.

Then, the blood pressure measurement device 408 extracts, for example, values at a particular timing in the pressure and the pulse wave, and associates the extracted values with each other to generate pulse wave information 2002.

Next, the blood pressure estimation device 101 executes the above-described processing on the basis of the pulse wave information 2002 calculated by the blood pressure measurement device 408 to estimate a blood pressure. At this time, the blood pressure estimation device 101 may transmit a control signal for an instruction of a control content to the pressure control unit 404.

The display unit 406 displays the blood pressure calculated by the blood pressure estimation device 101. The display unit 406 is an LCD (Liquid_Crystal_Display), an OLED (Organic_light-emitting_diode), an electronic paper, or the like. The electronic paper can be realized in accordance with, for example, a microcapsule type, an electron powder fluid type, a cholesteric liquid crystal type, an electrophoretic type, an electrowetting type, or the like.

According to the blood pressure estimation device 101 of the first exemplary embodiment, a blood pressure can be estimated with a high degree of accuracy. The reason is that even when pulse wave information includes an error to some extent, the blood pressure estimation device 101 reads a blood pressure associated with particular pulse wave information from blood pressure information and thereby reduces the error.

The blood pressure measurement device 408 may include an aspect in which the blood pressure estimation device 101, and the pulse wave measurement unit 402 and the pulse wave measurement unit 430 execute transmission/reception of pulse wave signals to/from each other via a communication network. An aspect in which the input unit 405 and the display unit 406 are located in the outside of the blood pressure measurement device 408 and are connected to the blood pressure measurement device 408 via a communication network may be employed.

Further, the specific region may be an upper arm, a wrist, or the like. When the specific region is, for example, a wrist, the pulse wave measurement unit 402 and the pulse wave measurement unit 403 may detect pulse waves via a radial artery.

The blood pressure measurement device 408 includes the blood pressure estimation device 101 and can therefore estimate a blood pressure with a high degree of accuracy.

<Second Exemplary Embodiment>

Next, a second exemplary embodiment of the present invention based on the above-described first exemplary embodiment will be described.

In the following description, characteristic parts according to the present exemplary embodiment will be mainly described and the same components as in the above-described first exemplary embodiment are assigned with the same reference signs, whereby overlapping description will be omitted.

Figure 12:
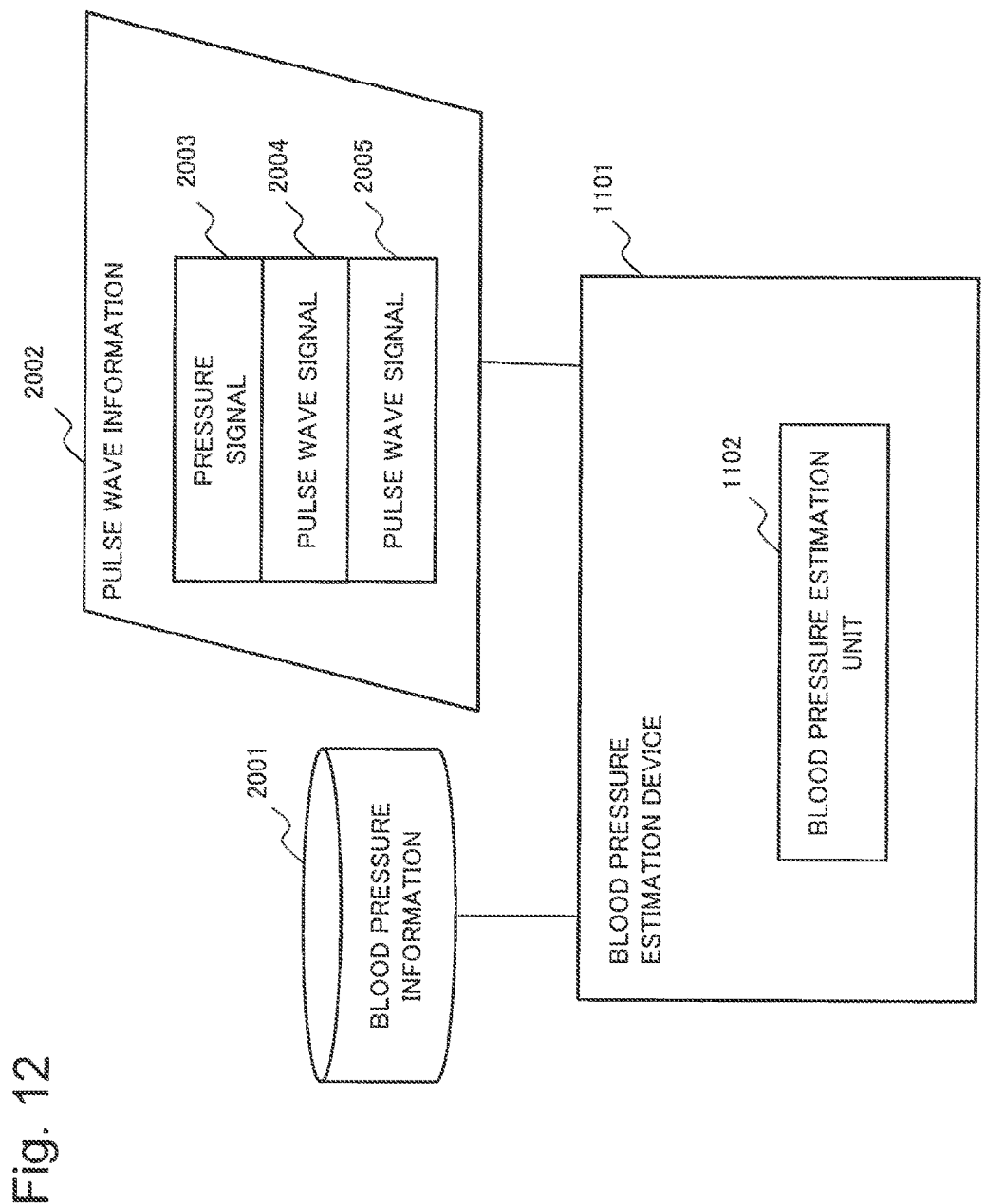
FIG. 12 is a block diagram illustrating components included in a blood pressure estimation device according to a second exemplary embodiment of the present invention.
Figure 13:
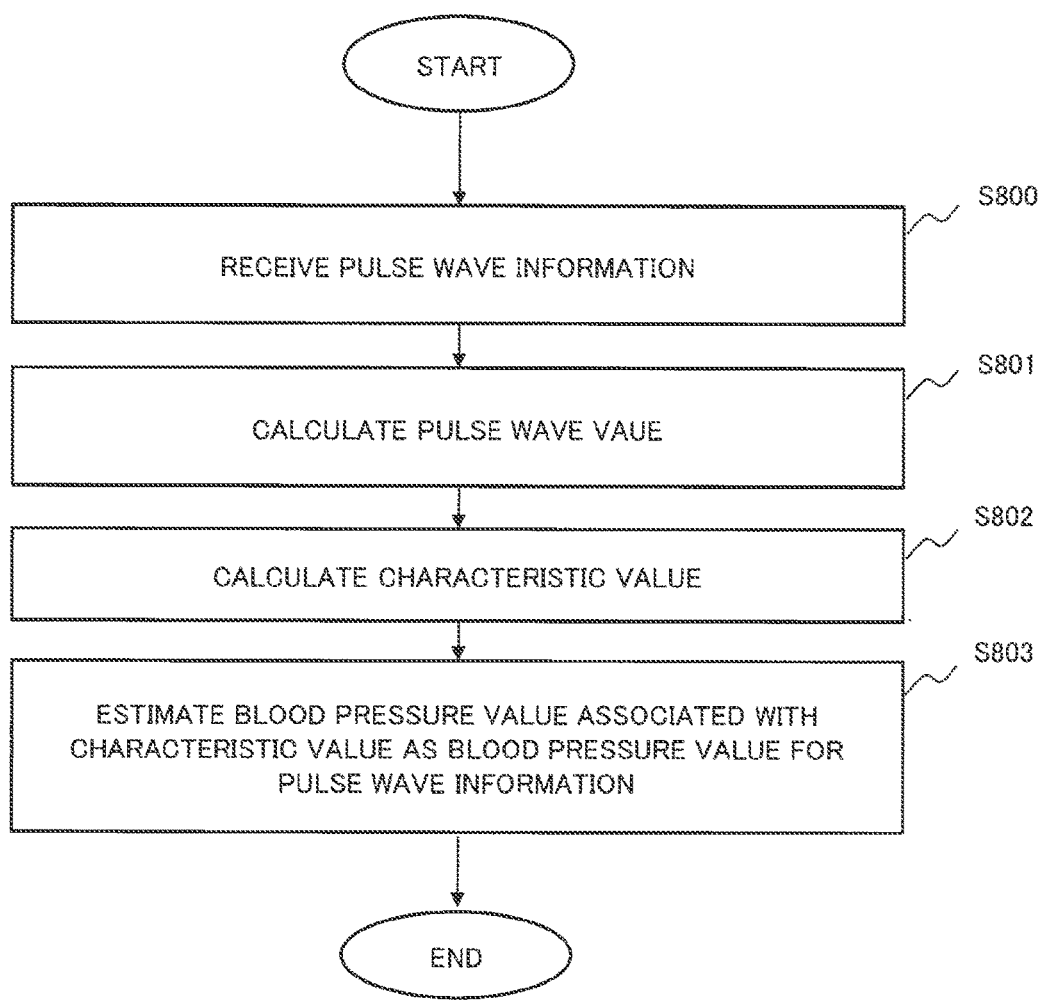
FIG. 13 is a flowchart illustrating a flow of processing in a blood pressure estimation device according to the second exemplary embodiment.

With reference to FIG. 12 and FIG. 13, components included in a blood pressure estimation device 1101 according to the second exemplary embodiment and processing executed by the blood pressure estimation device 1101 will be described. FIG. 12 is a block diagram illustrating the components included in the blood pressure estimation device 1101 according to the second exemplary embodiment of the present invention. FIG. 13 is a flowchart illustrating a flow of processing in the blood pressure estimation device 1101 according to the second exemplary embodiment.

The blood pressure estimation device 1101 according to the second exemplary embodiment includes a blood pressure estimation unit 1102.

The blood pressure estimation unit 1102 receives pulse wave information 2002 (i.e. a pressure signal 2003, a pulse wave signal 2004, and a pulse wave signal 2005) (step S800). The blood pressure estimation unit 1102 calculates pulse wave values for the received multiple pulse wave signals (i.e. the pulse wave signal 2004 and the pulse wave signal 2005) (step S801).

The pulse wave values are, for example, a pulse wave value 1 to a pulse wave value 6 listed below. Specifically:

An extremum (i.e. a local maximum value, a local minimum value, or both thereof) of a pulse wave signal, or a timing of an extremal value vicinity . . . (a pulse wave value 1)

An amplitude value of a pulse wave signal . . . (a pulse wave value 2),

A timing when a pulse wave signal rises (starts increasing) . . . (a pulse wave value 3), A timing when a pulse wave signal falls (starts decreasing) . . . (a pulse wave value 4), An amplitude of a pulse wave signal in a frequency space into which the pulse wave signal is converted . . . (a pulse wave value 5), and A phase of a pulse wave signal in a frequency space into which the pulse wave signal is converted . . . (a pulse wave value 6).

For example, "around the extremum" can be defined as a value that is within a particular rage from an extremum. The certain range may be a value calculated on the basis of a fact that a magnitude of an inclination (determined by calculating a differential or difference) to a target for which an extremum is calculated is smaller than a predetermined value. The certain range is not limited to the above-described example.

The blood pressure estimation unit 1102 calculates a pulse wave value 1 to a pulse wave value 4 in an area equivalent to one heartbeat in a pulse wave signal. The blood pressure estimation unit 1102 may extract, for example, a pulse wave signal having a particular cycle included in the pulse wave signal and calculate the pulse wave value 1 to the pulse wave value 4. Features of the pulse wave value 1 to the pulse wave value 4 are simplicity of calculation and short analysis time.

On the other hand, a pulse wave value 5 and a pulse wave value 6 are pulse wave values for a plurality of frequencies included in the pulse wave signal in the area equivalent to one heartbeat. Features of the pulse wave value 5 and the pulse wave value 6 are that a pulse wave value can be calculated even when various frequency components are included.

Since a case in which a pulse wave signal or a signal derived from the pulse wave signal via a differentiation, a difference, or the like of the pulse wave signal satisfies a predetermined condition needs to be defined as a pulse wave value, the pulse wave value is not limited to the above-described example.

Further, a method for converting a pulse wave signal into a frequency space (frequency area) includes, for example, short-time Fourier transformation, wavelet transformation, and the like. Short-time Fourier transformation, wavelet transformation, and the like are common techniques. Therefore, in the present exemplary embodiment, description thereof will be omitted.

With respect to the pulse wave value calculated by the blood pressure estimation unit 1102, there may be one pulse wave value or a plurality of pulse wave values.

Next, the blood pressure estimation unit 1102 calculates a difference between the pulse wave values calculated in step S801 for the pulse wave signal 2004 and the pulse wave signal 2005 as a characteristic value (step S802).

The blood pressure estimation unit 1102 calculates a difference between the pulse wave values or a ratio between the pulse wave values as the difference.

The blood pressure estimation unit 1102 may calculate, as the characteristic value, for example, a characteristic value 1 to a characteristic value 6 as listed below. Specifically:

A ratio between a pulse wave value 1 for the pulse wave signal 2004 and a pulse wave value 1 for the pulse wave signal 2005 . . . (a characteristic value 1), A difference between a pulse wave value 2 for the pulse wave signal 2004 and a pulse wave value 2 for the pulse wave signal 2005 . . . (a characteristic value 2), A difference between a pulse wave value 3 for the pulse wave signal 2004 and a pulse wave value 3 for the pulse wave signal 2005 . . . (a characteristic value 3), A difference between a pulse wave value 4 for the pulse wave signal 2004 and a pulse wave value 4 for the pulse wave signal 2005 . . . (a characteristic value 4), A ratio between a pulse wave value 5 for the pulse wave signal 2004 and a pulse wave value 5 for the pulse wave signal 2005 . . . (a characteristic value 5), and A difference between a pulse wave value 6 for the pulse wave signal 2004 and a pulse wave value 6 for the pulse wave signal 2005 . . . (a characteristic value 6).

Herein, the difference may be an absolute value of the difference. A difference to be detected may be a numerical value representing a gap such as a ratio, a difference, or the like. Therefore, the characteristic value calculated by the blood pressure estimation unit 1102 is not limited to the above-described example.

The blood pressure estimation unit 1102 associates the calculated characteristic value with a pressure signal 2003 at a timing when a pulse wave value as a basis of the characteristic value is calculated and calculates pulse wave information 2002.

In this case, in the pulse wave information 2002, a characteristic value calculated from multiple pulse wave signals is associated with a pressure unlike the information exemplified in FIG. 7.

The blood pressure estimation unit 1102 reads a blood pressure associated with the calculated pulse wave information 2002 in the blood pressure information 2001 and estimates a first blood pressure for the pulse wave information 2002 on the basis of the read blood pressure (step S803).

In the present exemplary embodiment, in pulse wave information included in the blood pressure information 2001, a pressure indicated by a pressure signal is associated with a characteristic value calculated by the blood pressure estimation unit 1102. In the pulse wave information, a characteristic value need not be always associated with a pressure and multiple pulse wave signals at a certain timing and a pressure signal may be associated with each other.

When, for example, there is one read blood pressure, the blood pressure estimation unit 1102 may estimate the blood pressure as a first blood pressure. Further, when a read blood pressure is determined in accordance with a degree of similarity, the blood pressure estimation unit 1102 may determine an average value as in determination of the blood pressure as a weighted average value in accordance with a degree of similarity to estimate a first blood pressure.

Figure 14:
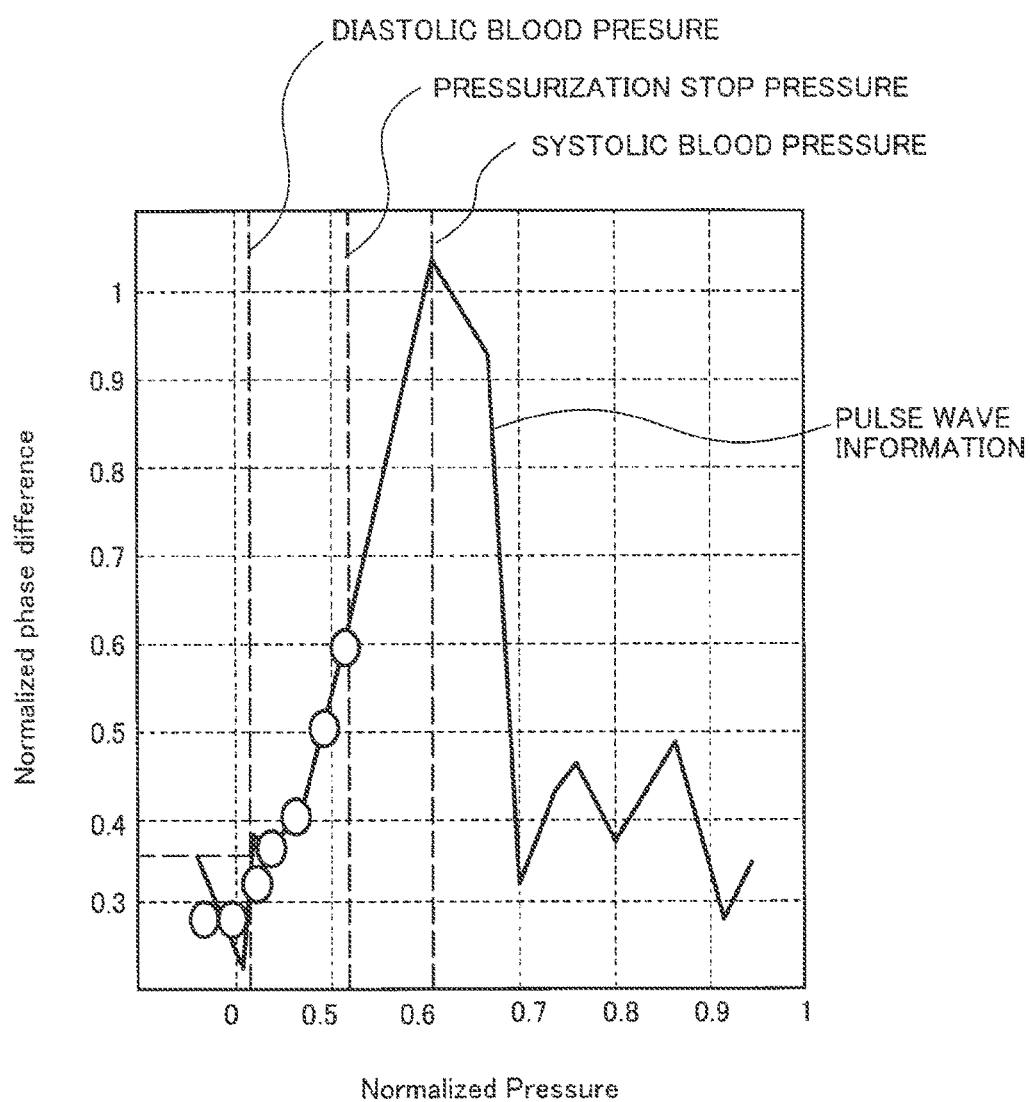
FIG. 14 is a diagram illustrating one example of a relation between a characteristic value and a pressure.

The characteristic value varies depending on a pressure applied upon measuring a pulse wave. There is, for example, a relation as illustrated in FIG. 14 between a characteristic value 6 and a pressure. FIG. 14 is a diagram illustrating one example of a relation between a characteristic value and a pressure. The horizontal axis of FIG. 14 represents a pressure indicated by the pressure signal 2003, and represents that the pressure becomes higher toward the right side. The vertical axis of FIG. 4 represents the characteristic value 6, and represents that the characteristic value 6 becomes larger toward the upper side. The characteristic value 6 starts rising from a vicinity where a pressure is a diastolic blood pressure and becomes largest (or substantially largest) in a vicinity where the pressure is a systolic blood pressure.

A circular mark "o" represents a characteristic value as described above. In other words, the blood pressure estimation unit 1102 uses a value in a circular mark "o" and thereby calculates pulse wave information exemplified in FIG. 7. A solid line, and a diastolic blood pressure and a systolic blood pressure (dotted-line portions) mean one piece of blood pressure information.

Figure 15:
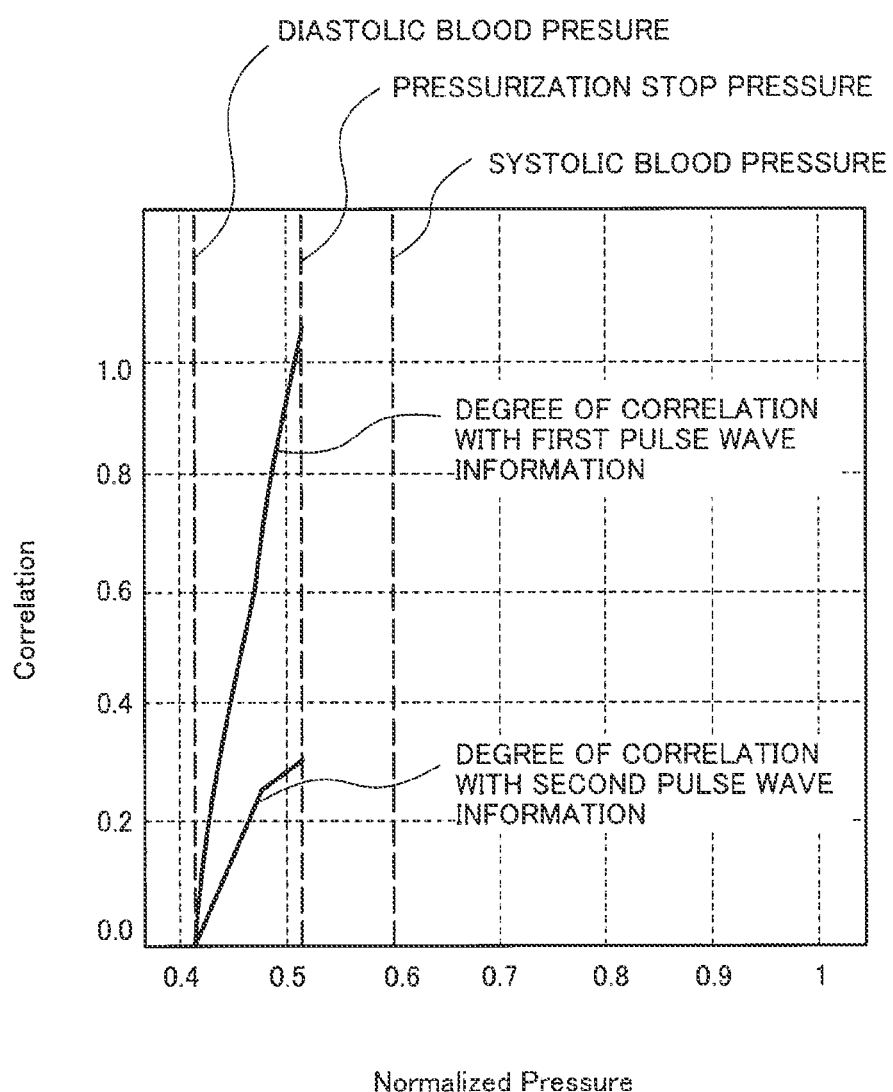
FIG. 15 is a diagram illustrating one example of pulse wave information.

FIG. 15 illustrates the pulse wave information illustrated in FIG. 14 and a degree of correlation obtained based on blood pressure information (a case of first blood pressure information or a case of second blood pressure information). The horizontal axis of FIG. 15 represents a normalized pressure, and represents that the pressure becomes higher toward the right side. The vertical axis of FIG. 15 represents a degree of correlation, and represents that the degree of correlation becomes higher toward the upper side.

For example, the blood pressure estimation unit 1102 calculates a degree of similarity R described below in accordance with Equation A. Specifically:

$$R=(\Sigma_i(x_i-x_m)\times(y_i-y_m))/a \qquad \text{(Equation A)}$$

wherein $y_i$ is a difference (e.g. a phase difference) of characteristic values at a particular blood pressure $P_i$ included in blood pressure information. The sign $x_i$ is a difference (e.g. a phase difference) of characteristic values at the particular blood pressure $P_i$ included in particular blood pressure information. The sign $y_m$ is an arithmetic average of phase differences $\{y_i\}$. The sign $x_m$ is an arithmetic average of phase differences $\{x_i\}$. The sign a is an optional constant. $\Sigma_i$ represents determining a sum for i.

The blood pressure estimation unit 1102 may normalize pulse wave information and pulse wave information in blood pressure information on the basis of a systolic blood pressure or the like and thereby calculate a degree of similarity on the basis of the normalized pulse wave information. In this case, the blood pressure estimation unit 1102 also coverts a blood pressure value associated with the pulse wave information on the basis of normalization of the pulse wave information. Therefore, the blood pressure estimation unit 1102 multiplies the blood pressure value and a normalization constant together to estimate a blood pressure for pulse wave information 2002.

The normalization makes it possible to reduce redundant pulse wave information in blood pressure information. In other words, the normalization makes it possible to lower a capacity of a database. Accordingly, a processing load in the blood pressure estimation unit 1102 is reduced.

The blood pressure estimation device 1101 according to the second exemplary embodiment includes components similar to those in the first exemplary embodiment, and therefore, effects similar to those in the first exemplary embodiment can be obtained from the second exemplary embodiment. In other words, according to the blood pressure estimation device 1101 of the second exemplary embodiment, a blood pressure can be estimated with a high degree of accuracy.

Hereinafter, an effect of reducing noise by calculating a difference between pulse wave values as a characteristic value used for calculating a degree of similarity will be described.

Movements in a person to be measured, vibrations transmitted from the outside, noise from a surrounding area, and the like are added to a pulse wave signal as noise signals.

For convenience of description, measured signals including noise signals are denoted by $S_1$ and $S_2$, and pulse wave signals related to the person to be measured are denoted by $P_1$ and $P_2$.

In this case, the measurement signals and the pulse wave signals have the relationships expressed by Equation 1 and Equation 2 below. Specifically, $$S_1 = P_1 \times a_1 + b_1 \quad \text{(Equation 1)}$$

$$S_2 = P_2 \times a_2 + b_2 \quad \text{(Equation 2)}$$

(where $a_1$ and $a_2$ respectively denote multiplication noise for the pulse wave signal $S_1$ and multiplication noise for the pulse wave signal $S_2$, and $b_1$ and $b_2$ respectively denote addition noise for the pulse wave signal $S_1$ and addition noise for the pulse wave signal $S_2$).

Here, k is defined according to Equation 3 below. Specifically, $$k = b_1/b_2 \quad \text{(Equation 3)}$$

Equation 4 below is established on the basis of Equation 1, Equation 2, and Equation 3 described above. Specifically, $$S_1 - k \times S_2 = P_1 \times a_1 - P_2 \times k \times a_2 \quad \text{(Equation 4)}$$

When $a_1$ and $a_2$ are sufficiently close to one (i.e., each multiplication noise is sufficiently small), or when a characteristic value that is not affected by any multiplication noise is extracted, $a_1$ and $a_2$ can be ignored, consequently reducing noise.

Here, m is defined according to Equation 5 below. Specifically, $$m = a_1/a_2 \quad \text{(Equation 5)}$$

Equation 6 below is established on the basis of Equation 1, Equation 2, and Equation 5 described above. Specifically, $$S_1/m/S_2 = (P_1 + b_1/a_1)/(P_2 + m \times b_2/a_1) \quad \text{(Equation 6)}$$

When $b_1$ and $b_2$ are sufficiently small with respect to $a_1$ and $a_2$, respectively, or when a characteristic value that is not affected by any addition noise is extracted, $a_1$ and $a_2$ can be ignored, consequently reducing noise.

Multiplication noise and addition noise are non-independently added to multiple pulse wave signals measured by multiple pulse wave measurement units located at positions close to each other. In this case, even when the values k and m are not determined, noise signal components can be reduced by calculating the difference.

Hence, the blood pressure estimation device 1101 according to the second exemplary embodiment can estimate blood pressure with a high degree of accuracy.

Figure 16:
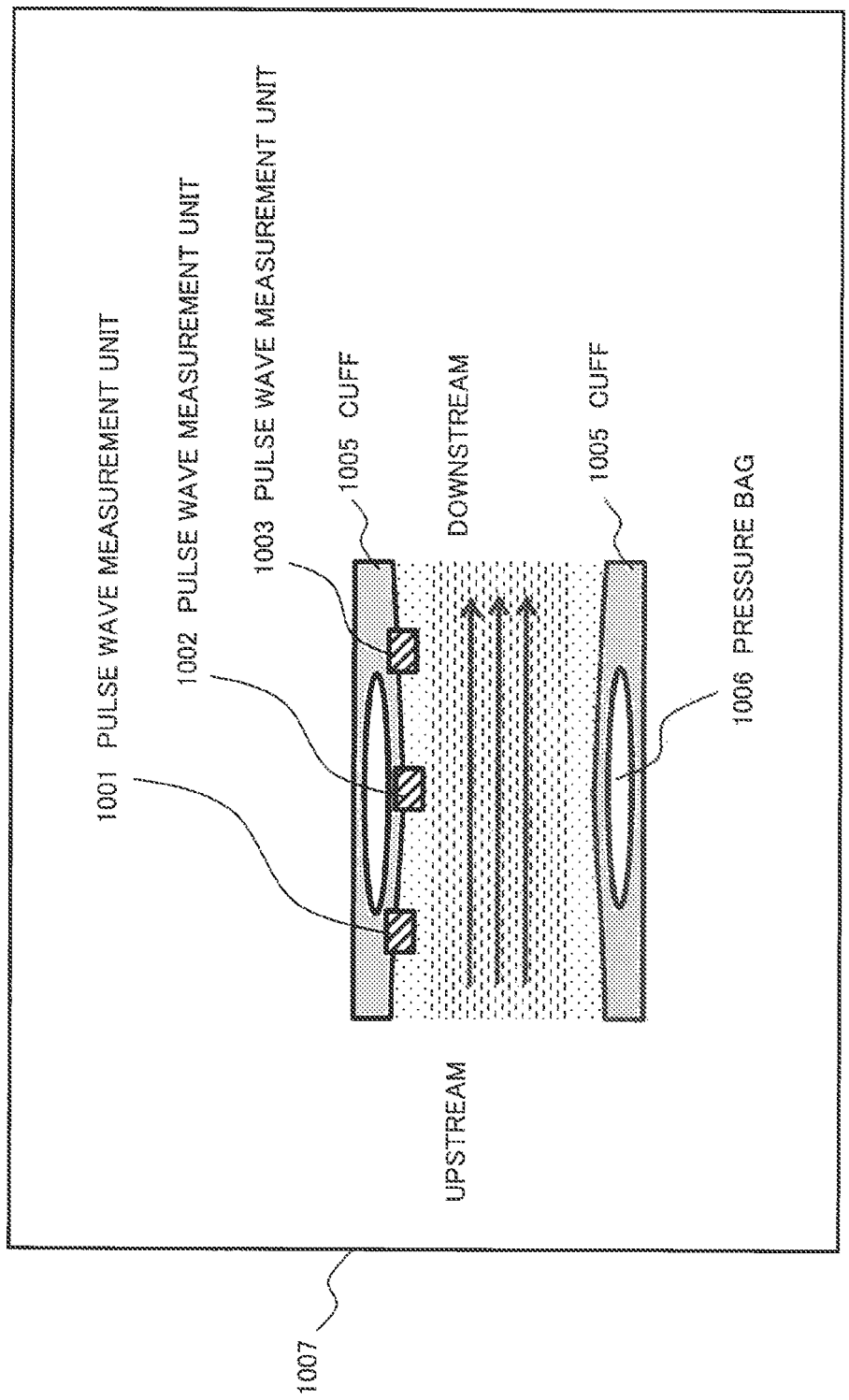
FIG. 16 is a diagram conceptually illustrating a position relation between a cuff and three pulse wave measurement units.

Further, with respect to the above-described pulse wave signals, there may be three or more pulse wave signals. In other words, as illustrated in FIG. 16, when a cuff 1005 also includes three pulse wave measurement units (a pulse wave measurement unit 1001, a pulse wave measurement unit 1002, and a pulse wave measurement unit 1003), the blood pressure estimation device 1101 can estimate a blood pressure in a manner similar to that in the above-described example. FIG. 16 is a diagram conceptually illustrating a position relation between the cuff 1005 and the three pulse wave measurement units.

For convenience of description, FIG. 16 includes a specific region and a blood flow and the like in the specific region. However, the blood pressure measurement device 1007 does not include any specific region and any blood flow and the like in a specific region.

The blood pressure measurement device 1007 includes a pulse wave measurement unit 1001, a pulse wave measurement unit 1002, a pulse wave measurement unit 1003, and the cuff 1005. The cuff 1005 may include a pressure bag 1006. At least two pulse wave measurement units of the pulse wave measurement unit 1001, the pulse wave measurement unit 1002, and the pulse wave measurement unit 1003 are located at positions so that pressurization center (or substantially center) in the shorter-side direction of the pressure application in the cuff 105 is located between the pulse wave measurement units.

Each of the pulse wave measurement unit 1001, the pulse wave measurement unit 1002, and the pulse wave measurement unit 1003 measures a pulse wave at the specific region.

Here, for convenience of description, measurement signals including noise are denoted by $S_1$, $S_2$, and $S_3$, and pulse signals are denoted by $P_1$, $P_2$, and $P_3$.

In this case, the measurement signals and the pulse wave signals have the relationships expressed by Equation 7 to Equation 9 below. Specifically, $$S_1 = P_1 \times a_1 + b_1 \quad \text{(Equation 7)}$$

$$S_2 = P_2 \times a_2 + b_2 \quad \text{(Equation 8)}$$

$$S_3 = P_3 \times a_3 + b_3 \quad \text{(Equation 9)}$$

(where $a_1$, $a_2$, and $a_3$ each denote multiplication noise for the corresponding pulse wave signal, and $b_1$, $b_2$, and $b_3$ each denote addition noise for the corresponding pulse wave signal).

Here, $k_1$ is defined according to Equation 10 below, and $k_2$ is defined according to Equation 11 below. Specifically, $$k_1 = b_1/b_2 \quad \text{(Equation 10)}$$

$$k_2 = b_1/b_3 \quad \text{(Equation 11)}$$

By calculating the difference between Equation 7 and Equation 8 and the difference between Equation 7 and Equation 9, Equation 12 and Equation 13 below are established. Specifically, $$S_1 - k_1 \times S_2 = P_1 \times a_1 - P_2 \times k_1 \times a_2 \quad \text{(Equation 12)}$$

$$S_1 - k_2 \times S_3 = P_1 \times a_1 - P_3 \times k_2 \times a_3 \quad \text{(Equation 13)}$$

By calculating (Equation 12)/(Equation 13), Equation 14 below is established. Specifically, $$(S_1-k_1\times S_2)/(S_1-k_2\times S_3)=(P_1-P_2\times k_1\times a_2/a_1)/(P_1-P_3\times k_2\times a_3/a_1) \quad \text{(Equation 14)}$$

Equation 14 indicates that, when $a_1$ is sufficiently close to $a_2$ and $a_3$ after the influences of the addition noises $b_1$, $b_2$, and $b_3$ are cancelled, the influences of the multiplication noises can be ignored. This indicates that noise can be reduced.

Further, the noise signals ($a_1$, $a_2$, $a_3$, $b_1$, $b_2$, and $b_3$) are non-independently added to multiple pulse signals measured by multiple pulse wave measurement units located at positions close to each other. Accordingly, Equation 14 indicates that the influences of these noises can be reduced by calculating the difference even when the values $k_1$ and $k_2$ are not determined.

Hence, the blood pressure estimation device 1101 according to the second exemplary embodiment can reduce the influences of noise by estimating blood pressure on the basis of three or more pulse wave signals as described above.

Figure 17:
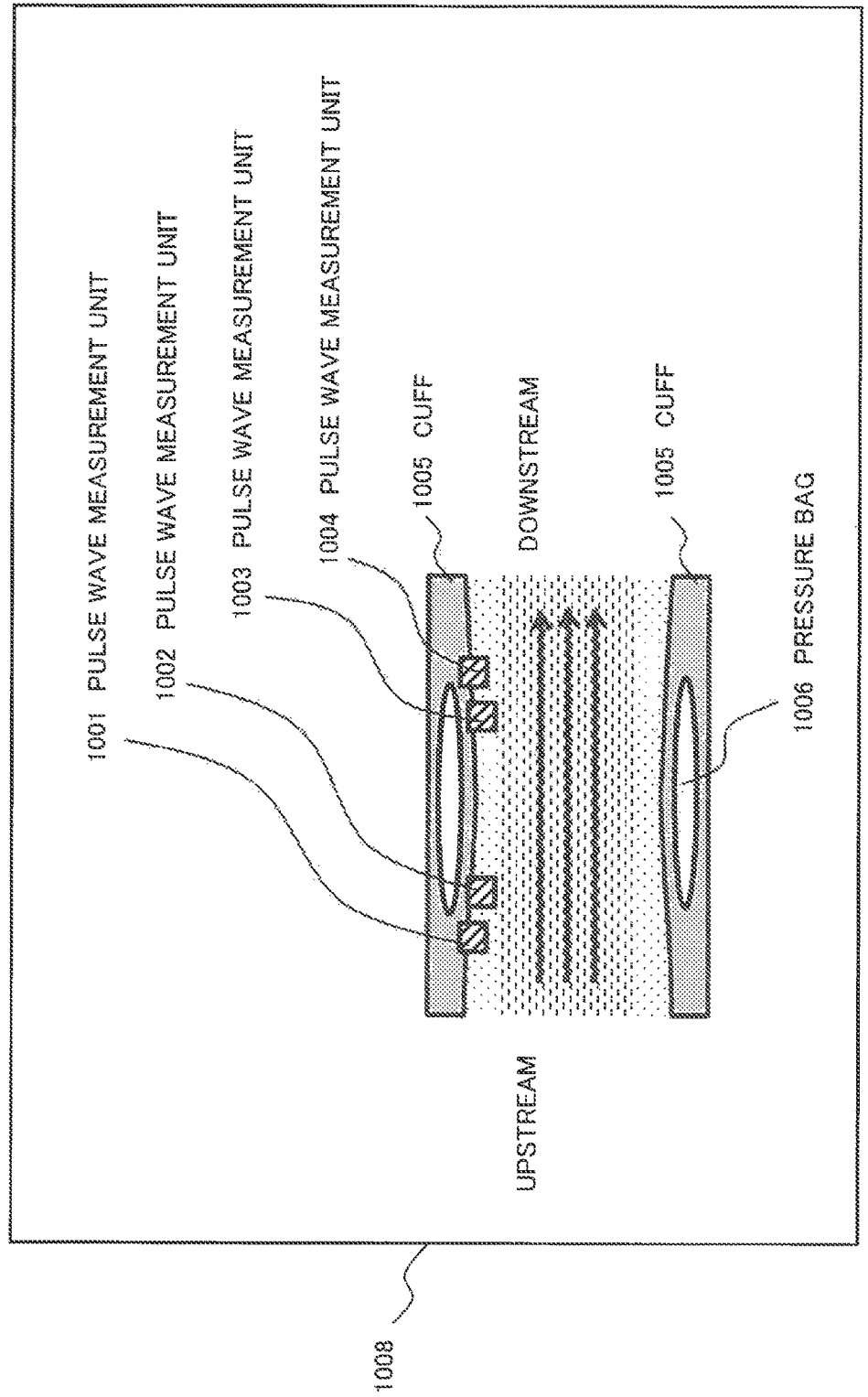
FIG. 17 is a diagram conceptually illustrating a position relation between a cuff and four pulse wave measurement units.

Further, as illustrated in FIG. 17, when the cuff 1005 also includes four pulse wave measurement units (a pulse wave measurement unit 1001, a pulse wave measurement unit 1002, a pulse wave measurement unit 1003, and a pulse wave measurement unit 1004), the blood pressure estimation device 1101 can estimate a blood pressure in a manner similar to that in the above-described example. FIG. 17 is a diagram conceptually illustrating a position relation between the cuff 1005 and the four pulse wave measurement units.

For convenience of description, FIG. 17 also illustrates a specific region and a blood flow in the specific region. However, a blood pressure measurement device 1008 does not include a specific region or a blood flow in the specific region.

The blood pressure measurement device 1008 includes the pulse wave measurement unit 1001, the pulse wave measurement unit 1002, the pulse wave measurement unit 1003, the pulse wave measurement unit 1004, and the cuff 1005. The cuff 1005 may include a pressure bag 1006. At least two pulse wave measurement units of the pulse wave measurement unit 1001, the pulse wave measurement unit 1002, the pulse wave measurement unit 1003, and the pulse wave measurement unit 1004 are located at positions that sandwich a pressurization center (or substantially the center) of a shorter side direction in the cuff 1005.

The pulse wave measurement unit 1001, the pulse wave measurement unit 1002, the pulse wave measurement unit 1003, and the pulse wave measurement unit 1004 each measure a pulse wave in a specific region.

The blood pressure estimation device 1101 estimates a blood pressure in a manner similar to the above-described processing by using the pulse wave measurement unit 1001, the pulse wave measurement unit 1002, the pulse wave measurement unit 1003, and the pulse wave measurement unit 1004.

Therefore, the blood pressure estimation device 1101 according to the second exemplary embodiment estimates a blood pressure on the basis of four or more pulse wave signals and can thereby reduce an influence of noise on the basis of a reason similar to the above-described reason.

<Third Exemplary Embodiment>

A third exemplary embodiment of the present invention based on the above-described first exemplary embodiment will be described.

In the following description, characteristic parts according to the present exemplary embodiment will be mainly described and the same components as in the above-described first exemplary embodiment are assigned with the same reference signs, whereby overlapping description will be omitted.

Figure 18:
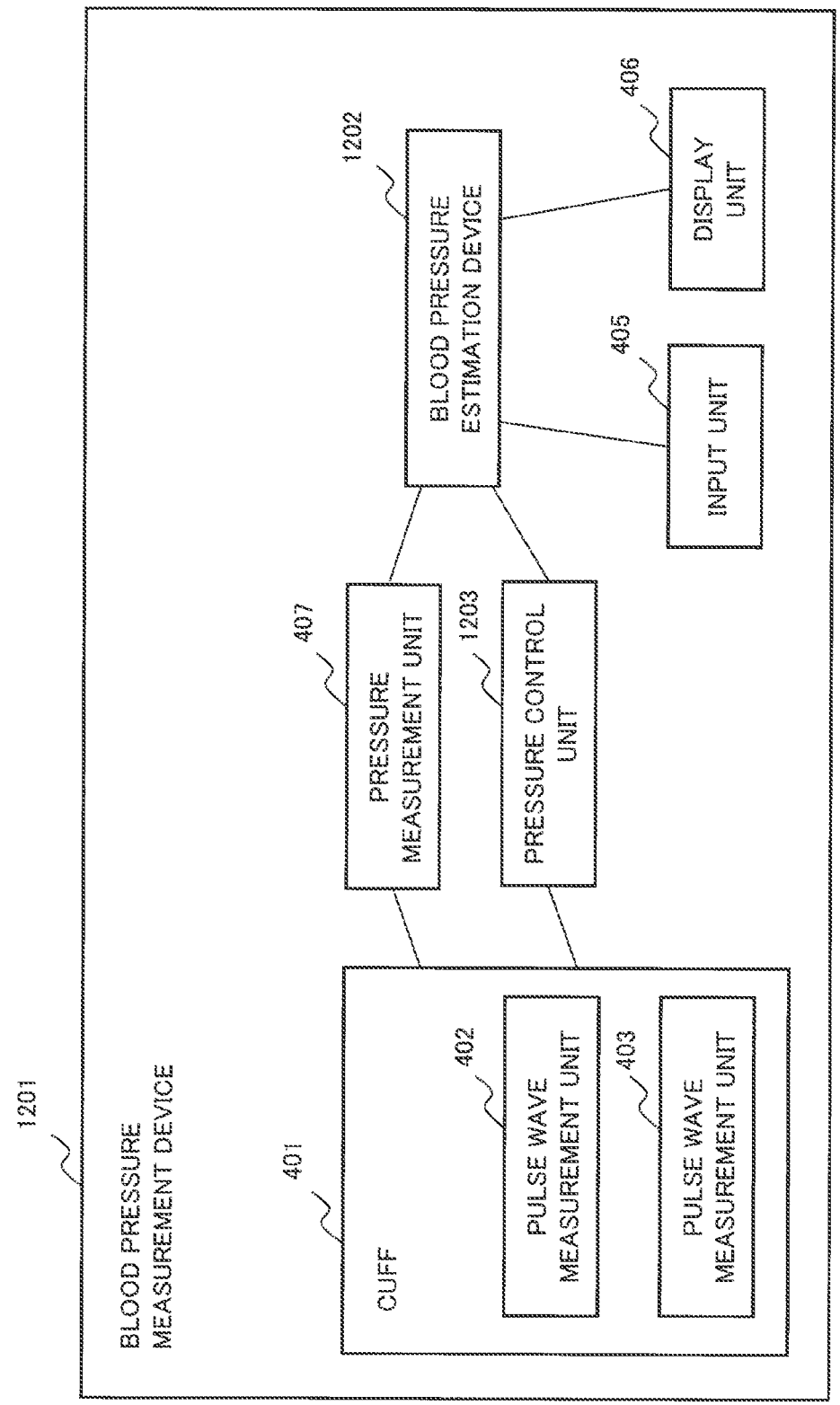
FIG. 18 is a block diagram illustrating components included in a blood pressure measurement device according to a third exemplary embodiment of the present invention.
Figure 19:
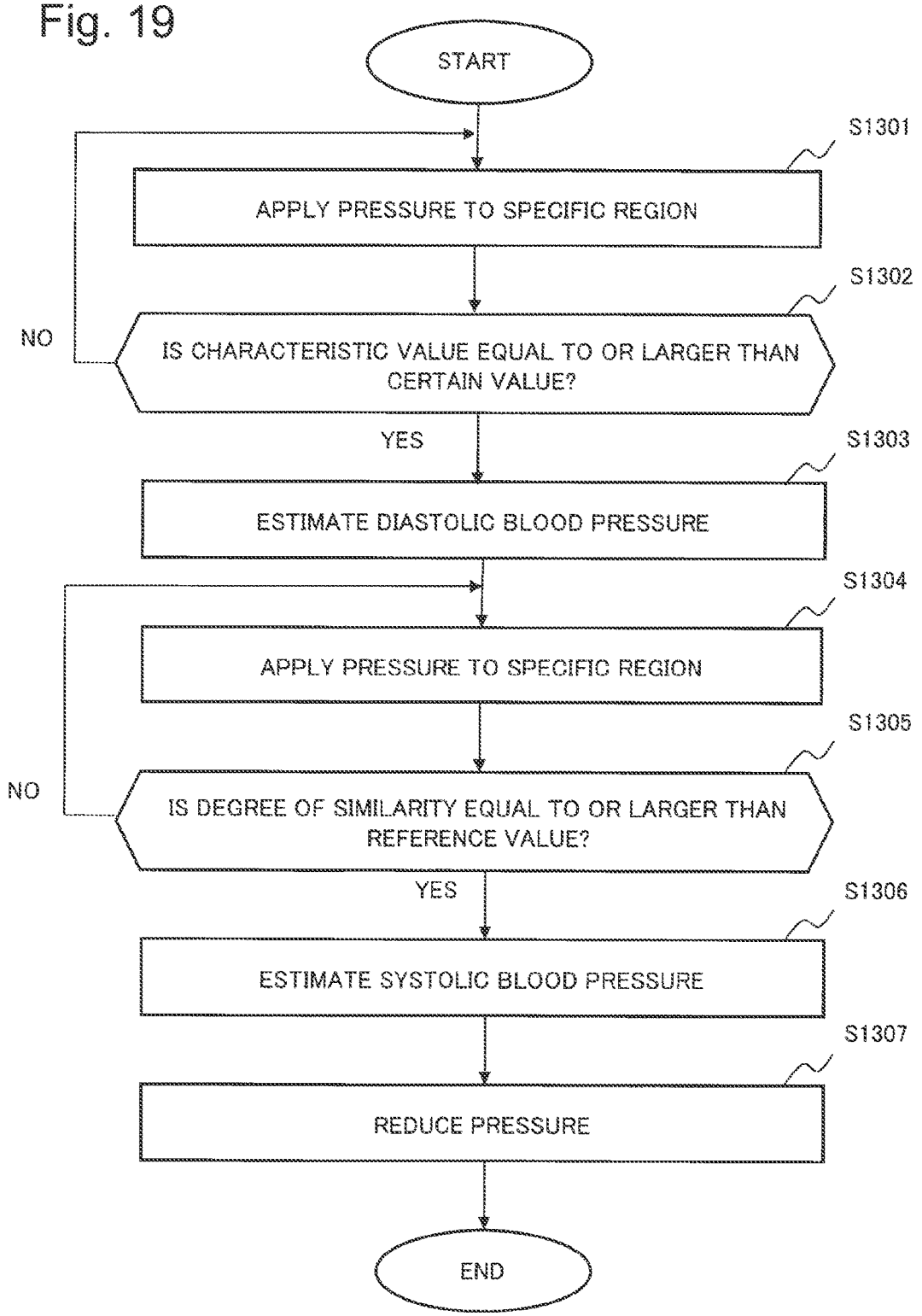
FIG. 19 is a flowchart illustrating a flow of processing in the blood pressure measurement device according to the third exemplary embodiment.

With reference to FIG. 18 and FIG. 19, components included in a blood pressure measurement device 1201 according to the third exemplary embodiment and processing executed by the blood pressure measurement device 1201 will be described. FIG. 18 is a block diagram illustrating the components included in the blood pressure measurement device 1201 according to the third exemplary embodiment of the present invention. FIG. 19 is a flowchart illustrating a flow of processing in the blood pressure measurement device 1201 according to the third exemplary embodiment.

The blood pressure measurement device 1201 includes a cuff 401, a pulse wave measurement unit 402, a pulse wave measurement unit 403, a pressure measurement unit 407, a pressure control unit 1203, an input unit 405, a display unit 406, and a blood pressure estimation device 1202.

First, the pressure control unit 1203 executes control for increasing an internal pressure of the cuff 401 in accordance with a start of measurement (step S1301). The pressure measurement unit 407 measures a pressure in a process of pressurization and transmits the measured pressure to the blood pressure estimation device 1202 as a pressure signal 2003. Further, the pulse wave measurement unit 402 and the pulse wave measurement unit 403 measure pulse waves in specific regions and transmit the measured pulse waves to the blood pressure estimation device 1202 as pulse wave signals (i.e. a pulse wave signal 2004 and a pulse wave signal 2005).

The blood pressure estimation device 1202 then receives the pressure signal 2003 and the pulse wave signals, and calculates a characteristic value on the basis of the received pressure signal 2003 and the received pulse wave signals. Next, the blood pressure estimation device 1202 determines whether the calculated characteristic value is equal to or larger than a predetermined value (step S1302).

When determining that the characteristic value is equal to or larger than the predetermined value (YES in step S1302), the blood pressure estimation device 1202 estimates a pressure in the pressure signal as a diastolic blood pressure (step S1303). The blood pressure estimation device 1202 transmits a control signal for increasing a pressure to the pressure control unit 1203, when determining that the characteristic value is smaller than the predetermined value (NO in step S1302). The pressure control unit 1203 receives the control signal and executes control for increasing the internal pressure of the cuff 401 in accordance with the received control signal (step S1301).

The blood pressure estimation device 1202 transmits a control signal for increasing a pressure to the pressure control unit 1203 after estimating the diastolic blood pressure. The pressure control unit 1203 receives the control signal and executes control for increasing the internal pressure of the cuff 401 in accordance with the received control signal (step S1304).

Next, the blood pressure estimation device 1202 receives a pressure signal 2003 and pulse wave signals after pressurization and calculates characteristic values on the basis of the received pressure signal and the received pulse wave signals. Then, the blood pressure estimation device 1202 calculates a degree of similarity from the calculated characteristic values and determines whether the degree of similarity is equal to or larger than a reference value (step S1305).

When determining that the degree of similarity is equal to or larger than the reference value (YES in step S1305), the blood pressure estimation device 1202 estimates a pressure in the pressure signal as a systolic blood pressure (step S1306). The blood pressure estimation device 1202 transmits a control signal for increasing a pressure to the pressure control unit 1203, when determining that the degree of similarity is not equal to or larger than the reference value (NO in step S1305). The pressure control unit 1203 receives the control signal and executes control for increasing the internal pressure of the cuff 401 in accordance with the received control signal (step S1304).

The blood pressure estimation device 1202 transmits a second control signal for reducing a pressure to the pressure control unit 1203, after calculating the systolic blood pressure. The pressure control unit 1203 receives the second control signal and executes control for reducing the internal pressure of the cuff 401 in accordance with the received second control signal (step S1307).

The blood pressure estimation device 1201 according to the third exemplary embodiment includes components similar to the blood pressure estimation device 101 according to the first exemplary embodiment, and therefore, effects similar to those in the first exemplary embodiment can be obtained from the third exemplary embodiment. In other words, according to the blood pressure estimation device 1201 of the third exemplary embodiment, a blood pressure can be estimated with a high degree of accuracy.

Figure 20A:
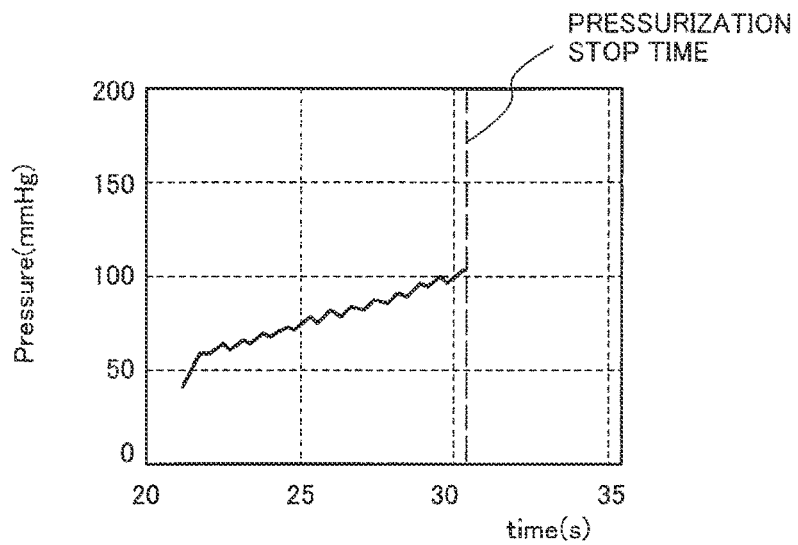
FIG. 20A is a diagram illustrating one example of a pressure signal measured by a pressure measurement unit.
Figure 20B:
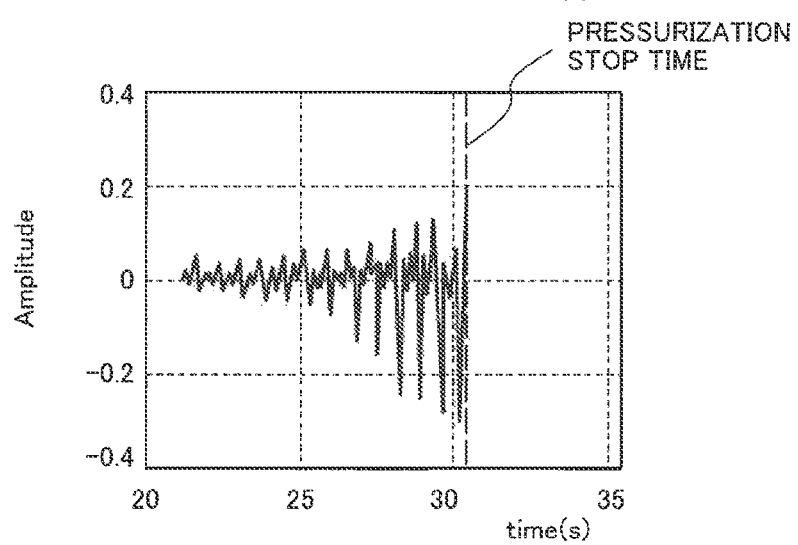
FIG. 20B is a diagram illustrating one example of a pulse wave signal measured at upstream by a pulse wave measurement unit.
Figure 20C:
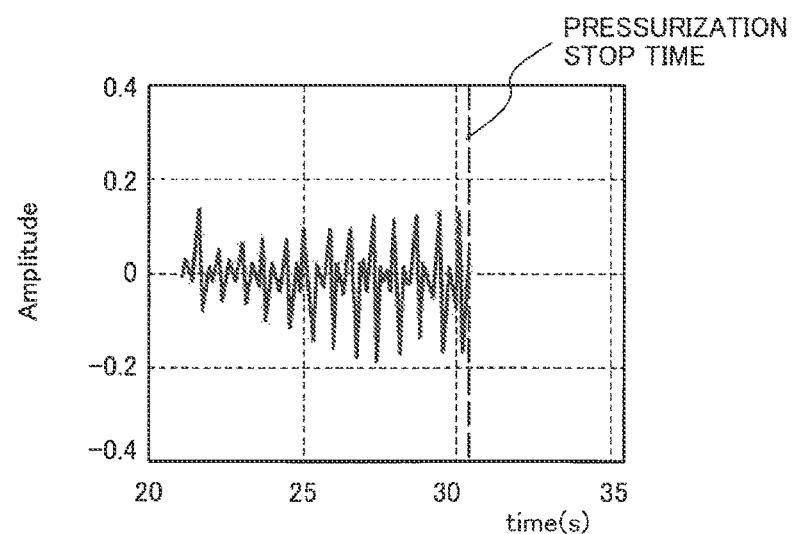
FIG. 20C is a diagram illustrating one example of a pulse wave signal measured at downstream by a pulse wave measurement unit.

The pressure measurement unit 407, the pulse wave measurement unit 402, and the pulse wave measurement unit 403 measure a pressure signal and pulse wave signals illustrated in FIG. 20A to FIG. 20C, respectively. FIG. 20A is a diagram illustrating one example of a pressure signal measured by the pressure measurement unit 407. FIG. 20B is a diagram illustrating one example of a pulse wave signal (hereinafter, expressed as a "pulse wave signal A") measured by the pulse wave measurement unit 402. FIG. 20C is a diagram illustrating one example of a pulse wave signal (hereinafter, expressed as a "pulse wave signal B") measured by the pulse wave measurement unit 403. Further, each horizontal axis in FIG. 20A to FIG. 20C represents time, and represents a later time at a rightward position. The vertical axis of FIG. 20A represents a pressure, and represents that the pressure becomes higher toward the upper side. The vertical axis of FIG. 20B and FIG. 20C represents an amplitude of a pulse wave, and represents that the amplitude of a pulse wave becomes higher toward the upper side or the lower side and becomes lower toward 0. A pressurization stop time represents a time when pressurization is stopped.

Figure 21A:
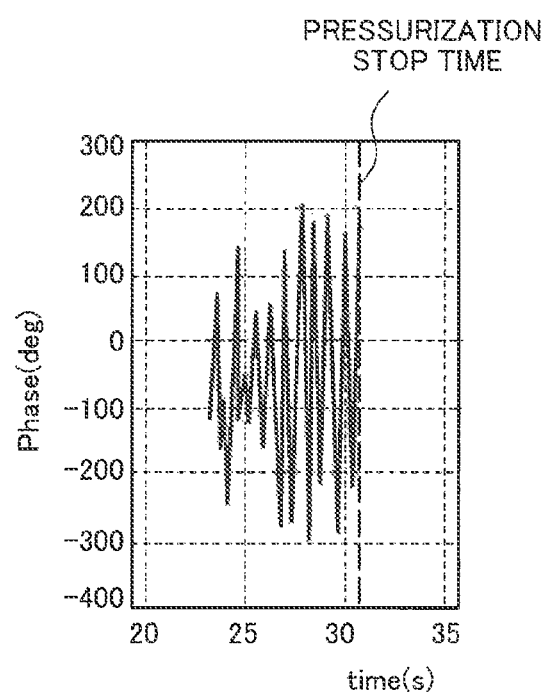
FIG. 21A is a diagram illustrating a phase as one example of a pulse wave value calculated via Fourier transform of a pulse wave signal.
Figure 21B:
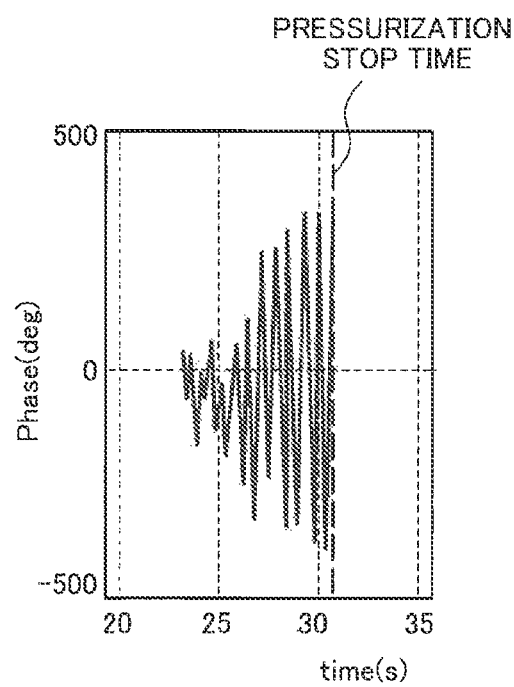
FIG. 21B is a diagram illustrating a phase as one example of a pulse wave value calculated via Fourier transform of a pulse wave signal.

The blood pressure estimation device 1202 receives the pulse wave signal A and the pulse wave signal B and calculate Fourier transform of the received pulse wave signals. In the present exemplary embodiment, it is assumed that Fourier transform of a pulse wave in one heartbeat is calculated. In this case, the blood pressure estimation device 1202 calculate Fourier transform of the pulse wave signal A and Fourier transform of the pulse wave signal B to calculate pulse wave values illustrated in FIG. 21A and FIG. 21B. FIG. 21A and FIG. 21B each are a diagram illustrating a phase as one example of a pulse wave value calculated via Fourier transform of a pulse wave signal.

Figure 22:
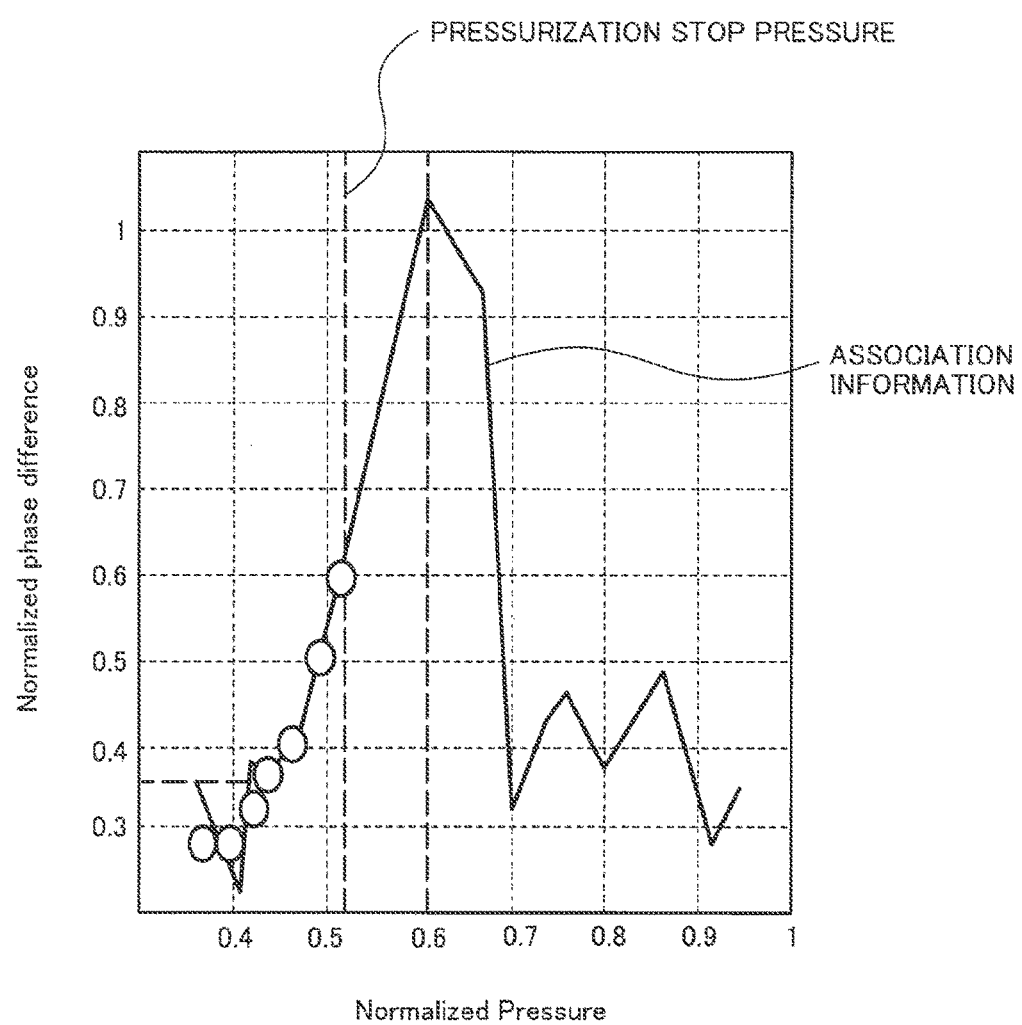
FIG. 22 is a diagram illustrating one example of a relation between a characteristic value and a pressure.

The blood pressure estimation device 1202 calculates a characteristic value, for example, as exemplified in FIG. 22 on the basis of the calculated pulse wave value. FIG. 22 is a diagram illustrating one example of a relation between a characteristic value and a pressure. A circular mark "o" of FIG. 22 represents one example of the calculated characteristic value.

The blood pressure estimation device 1202 calculates, for example, a pulse wave value at a predetermined timing on the basis of the pulse wave signal 2004 and further calculates a pulse wave value at the predetermined timing on the basis of the pulse wave signal 2005. The blood pressure estimation device 1202 calculates characteristic values on the basis of the two pulse wave values, associates the calculated characteristic values with a blood pressure at the predetermined timing, and thereby generates association information. Similarly, the blood pressure estimation device 1202 generates association information (expressed as "first association information" for convenience of description) also for pulse wave information included in blood pressure information 2001.

For convenience of description, with respect to the blood pressure information 2001, it is assumed that there are a plurality of pieces of blood pressure information 2001. In this case, the blood pressure estimation device 1202 generates first association information for each of the pieces of blood pressure information.

Figure 23:
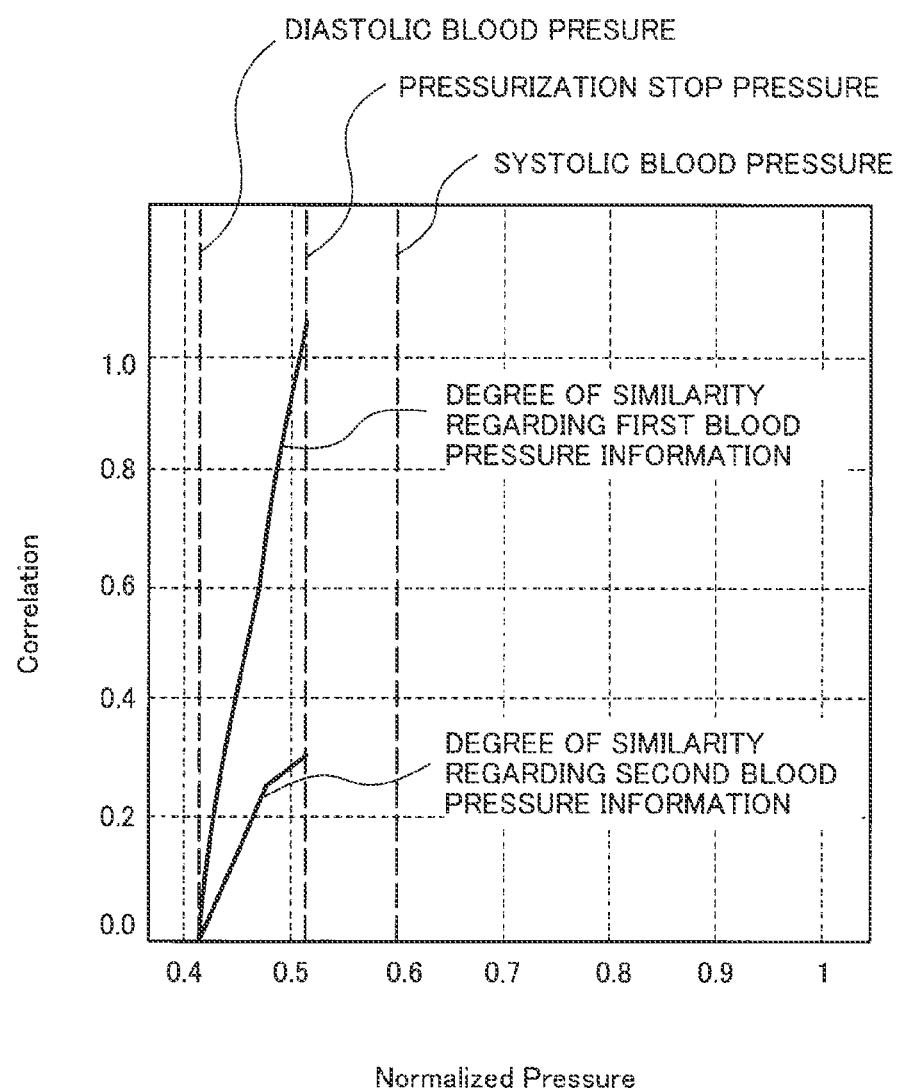
FIG. 23 is a diagram illustrating one example of a calculated degree of similarity.

Thereafter, the blood pressure estimation device 1202 calculates a degree of similarity (e.g. FIG. 23) between the association information and the first association information, for example, in accordance with Equation A. FIG. 23 is a diagram illustrating one example of the calculated degree of similarity. FIG. 23 illustrates degrees of similarity calculated for two pieces of blood pressure information (e.g. the first blood pressure information and the second blood pressure information). When, for example, with respect to particular blood pressure information having a highest degree of similarity between the association information and the first association information in a plurality of pieces of blood pressure information, the degree of similarity is equal to or larger than a reference value, the blood pressure estimation device 1202 estimates a systolic blood pressure on the basis of the particular blood pressure information. The pressure control unit 1203 then executes control for reducing the internal pressure of the cuff 401.

The blood pressure measurement device 1201 applies a pressure near a systolic blood pressure to estimate a systolic blood pressure while increasing the internal pressure of the cuff 401. The blood pressure measurement device 1201 reduces the internal pressure in accordance with completion of the estimation.

On the other hand, a common blood pressure measurement device estimates a systolic blood pressure while reducing the internal pressure of the cuff 401 after applying a pressure sufficiently higher than the systolic blood pressure.

Therefore, according to the blood pressure measurement device 1201 of the present exemplary embodiment, a systolic blood pressure can be measured at a pressure lower than that for the common blood pressure measurement device.

In other words, according to the blood pressure measurement device 1201 of the present exemplary embodiment, it is possible to shorten a measurement time and further reduce a burden imposed to a person to be measured.

<Fourth Exemplary Embodiment>

Next, a fourth exemplary embodiment of the present invention based on the above-described third exemplary embodiment will be described.

In the following description, characteristic parts according to the present exemplary embodiment will be mainly described and the same components as in the above-described third exemplary embodiment are assigned with the same reference signs, whereby overlapping description will be omitted.

Figure 24:
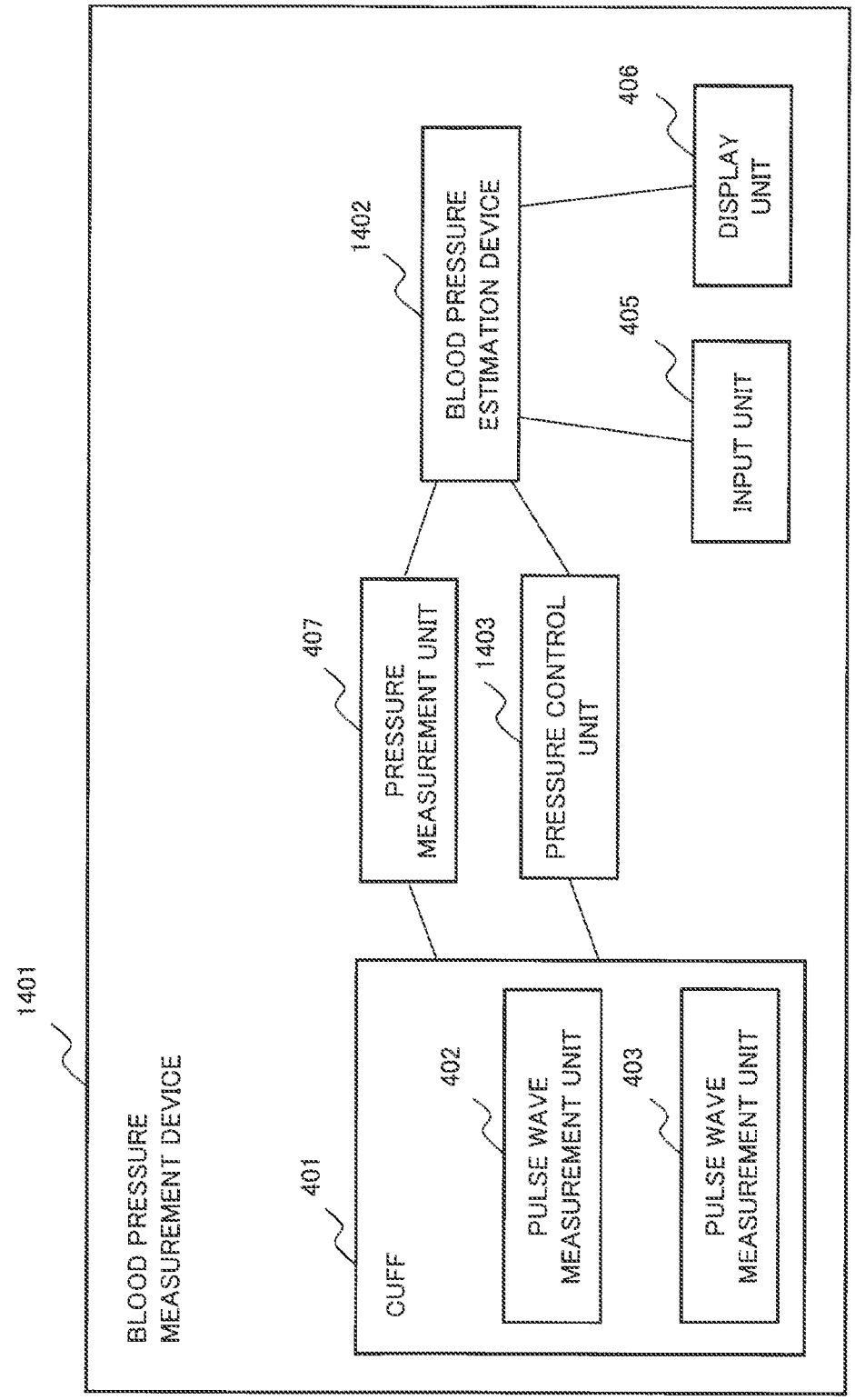
FIG. 24 is a block diagram illustrating components included in a blood pressure measurement device according to a fourth exemplary embodiment of the present invention.
Figure 25:
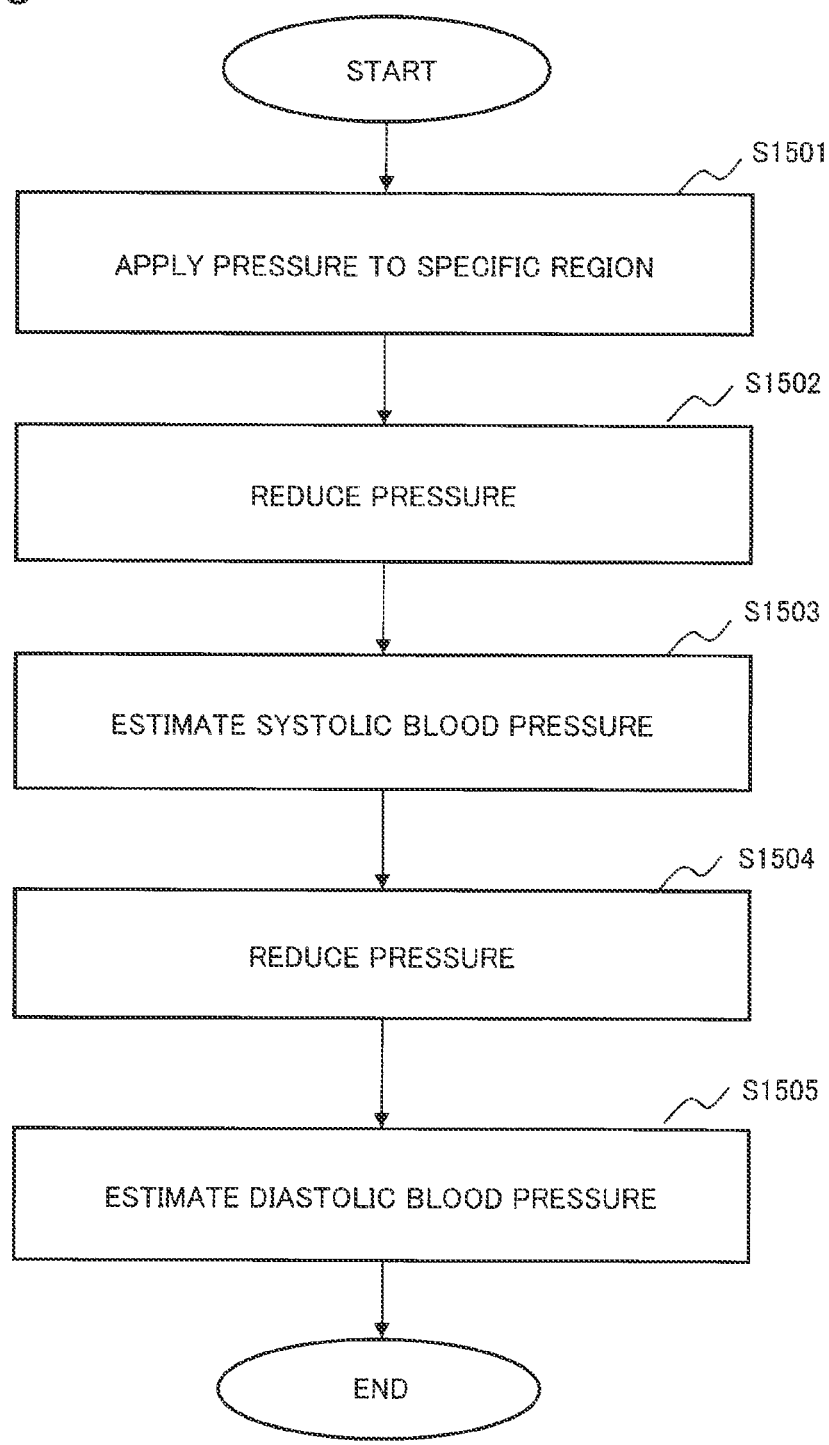
FIG. 25 is a flowchart illustrating a flow of processing in a blood pressure measurement device according to the fourth exemplary embodiment.

With reference to FIG. 24 and FIG. 25, components included in a blood pressure measurement device 1401 according to the fourth exemplary embodiment and processing executed by the blood pressure measurement device 1401 will be described. FIG. 24 is a block diagram illustrating the components included in the blood pressure measurement device 1401 according to the fourth exemplary embodiment of the present invention. FIG. 25 is a flowchart illustrating a flow of processing in the blood pressure measurement device 1401 according to the fourth exemplary embodiment.

The blood pressure measurement device 1401 includes a cuff 401, a pulse wave measurement unit 402, a pulse wave measurement unit 403, a pressure measurement unit 407, a pressure control unit 1403, an input unit 405, a display unit 406, and a blood pressure estimation device 1402.

First, the pressure control unit 1403 executes control for increasing an internal pressure of the cuff 401 up to a predetermined pressure (a pressure sufficiently higher than a common systolic blood pressure), in accordance with a start of measurement (step S1501). Then, the pressure control unit 1403 executes control for reducing the pressure (step S1502). In a process of the depressurization, the pressure measurement unit 407 measures the internal pressure of the cuff 401 and transmits the measured pressure to the blood pressure estimation device 1402 as a pressure signal 2003. Further, the pulse wave measurement unit 402 and the pulse wave measurement unit 403 measure pulse waves in specific regions and transmit the measured pulse waves to the blood pressure estimation device 1402 as pulse wave signals.

The pressure control unit 1403 executes control in step S1501 and step S1502, and therefore, a pressure decreases with a lapse of time.

Then, the blood pressure estimation device 1402 calculates pulse wave values and calculates characteristic values on the basis of the calculated pulse wave values.

The blood pressure estimation device 1402 calculates a degree of similarity on the basis of the calculated characteristic values. When the calculated degree of similarity is equal to or larger than a reference value, the blood pressure estimation device 1402 estimates a systolic blood pressure on the basis of the degree of similarity (step S1503) and estimates a diastolic blood pressure on the basis of the calculated degree of similarity compared with the reference value (step S1505). In this case, the pressure control unit 1403 continues to execute control for reducing the pressure (step S1504).

The blood pressure measurement device 1401 according to the fourth exemplary embodiment includes components similar to those in the first exemplary embodiment, and therefore, effects similar to those in the first exemplary embodiment can be obtained from the fourth exemplary embodiment. In other words, according to the blood pressure estimation device 1401 according to the fourth exemplary embodiment, a blood pressure can be estimated with a high degree of accuracy.

The blood pressure estimation device 1401 sufficiently performs pressurization and thereafter measures a pulse wave in a depressurization process to estimate a blood pressure. As a result, according to the blood pressure measurement device 1401 according to the present exemplary embodiment, a pulse wave can be measured at a pressure of a wider range, and therefore, a blood pressure can be estimated with a higher degree of accuracy.

It is not always necessary for the blood pressure measurement device 1401 to estimate a blood pressure only in a process of pressurization and only in a process of depressurization, as described in the third exemplary embodiment and the fourth exemplary embodiment. The blood pressure measurement device 1401 may control a pressure on the basis of a degree of similarity calculated by the blood pressure estimation device 1402.

When, for example, a degree of similarity does not exceed a reference value even with a decrease in an internal pressure of the cuff 401, it is difficult to determine a systolic blood pressure, and therefore, the blood pressure control unit 1403 may execute control for increasing the internal pressure of the cuff 401. In this case, while the pressure control unit 1403 repeats pressurization and depressurization, the blood pressure estimation device 1402 estimates a systolic blood pressure and a diastolic blood pressure.

When the above-described processing is executed, a systolic blood pressure can be searched via repetition of a process of pressurization and a process of depressurization, and therefore, according to the blood pressure measurement device 1401, a blood pressure can be estimated with a higher degree of accuracy.

Further, the blood pressure measurement device 1401 may estimate a blood pressure in a process of pressurization and further estimate a blood pressure in a process of depressurization. In this case, the blood pressure measurement device 1401 estimates a blood pressure by processing for averaging the two blood pressure or the like.

Further, the blood pressure measurement device 1401 may estimate blood pressures in the respective processes via repetition of a process of pressurization and a process of depressurization. In this case, the blood pressure measurement device 1401 estimates a blood pressure by processing for averaging the estimated blood pressures or the like.

When the above-described processing is executed, a blood pressure estimated by averaging blood pressures calculated in a process of repetition of pressurization and depressurization becomes a more accurate. In other words, according to the blood pressure measurement device 1401, (Hardware Configuration Example)

A configuration example of hardware resources that realize a blood pressure estimation device in the above-described exemplary embodiments of the present invention using a single calculation processing apparatus (an information processing apparatus or a computer) will be described. However, the pressure estimation device may be realized using physically or functionally at least two calculation processing apparatuses. Further, the pressure estimation device may be realized as a dedicated apparatus.

Figure 26:
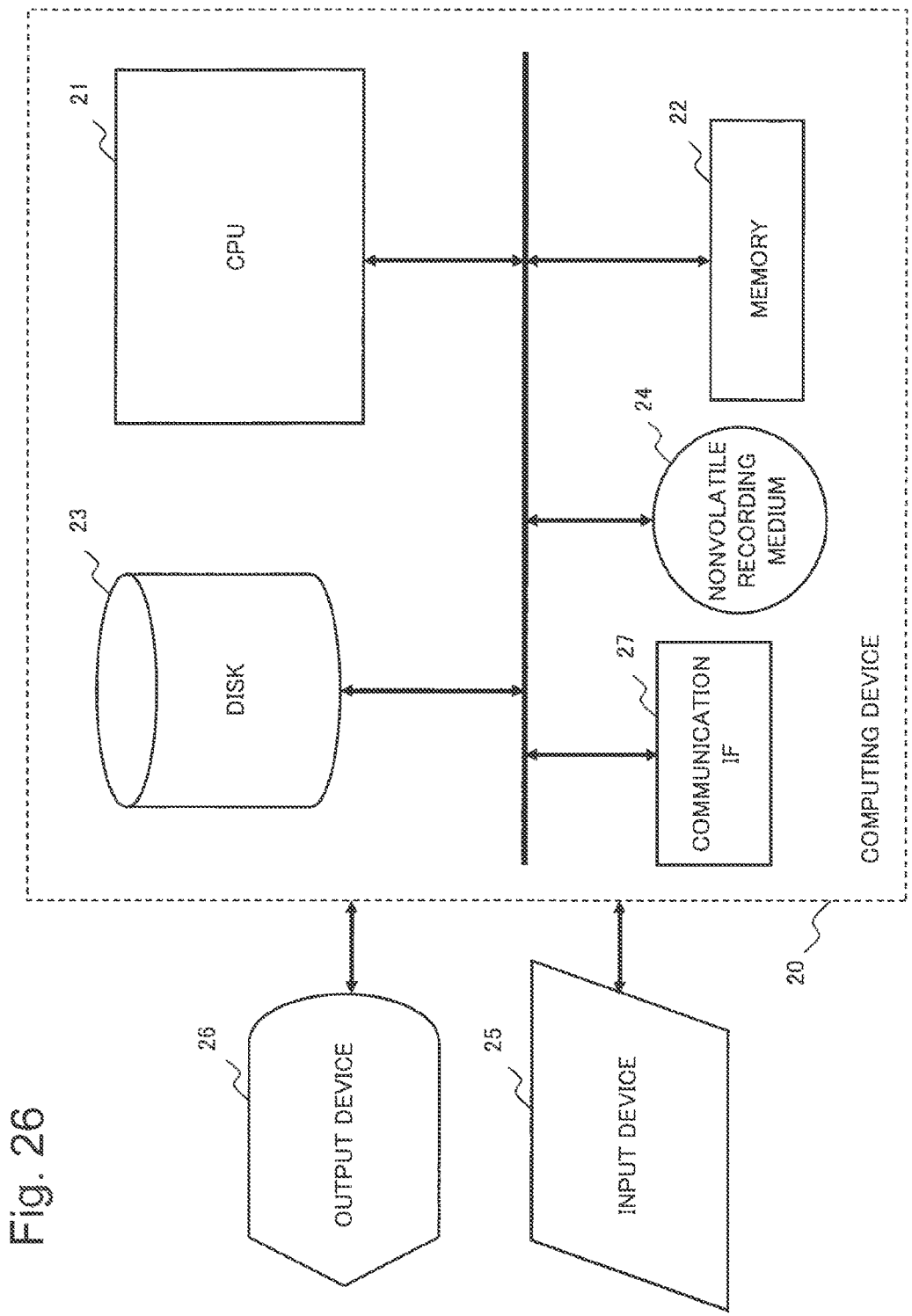
FIG. 26 is a block diagram schematically illustrating a hardware configuration of a calculation processing apparatus capable of realizing a blood pressure estimation device or a pressure controlling unit according to each exemplary embodiment of the present invention.

FIG. 26 is a block diagram schematically illustrating a hardware configuration of a calculation processing apparatus capable of realizing the blood pressure estimation device according to each of the first exemplary embodiment to the four exemplary embodiment or a pressure controlling unit in the blood pressure measurement device. A calculation processing apparatus 20 includes a central processing unit (CPU) 21, a memory 22, a disc 23, a non-transitory recording medium 24, an input apparatus 25, an output apparatus 26, and a communication interface (hereinafter, expressed as a "communication I/F") 27. The calculation processing apparatus 20 can execute transmission/reception of information to/from another calculation processing apparatus and a communication apparatus via the communication I/F 27.

The non-transitory recording medium 24 is, for example, a computer-readable Compact Disc, Digital_Versatile_Disc. The non-transitory recording medium 24 is, for example, Universal Serial Bus (USB) memory, or Solid State Drive. The non-transitory recording medium 24 allows a related program to be holdable and portable without power supply. The non-transitory recording medium 24 is not limited to the above-described media. Further, a related program can be carried via a communication network by way of the communication I/F 27 instead of the non-transitory medium 24.

In other words, the CPU 21 copies, on the memory 22, a software program (a computer program: hereinafter, referred to simply as a "program") stored by the disc 23 when executing the program and executes arithmetic processing. The CPU 21 reads data necessary for program execution from the memory 22. When display is needed, the CPU 21 displays an output result on the output apparatus 26. When a program is input from the outside, the CPU 21 reads the program from the input apparatus 25. The CPU 21 interprets and executes a blood pressure estimation program present on the memory 22 corresponding to a function (processing) indicated by each unit illustrated in FIG. 1, FIG. 8, FIG. 12, FIG. 18, or FIG. 24 described above or an blood pressure estimation program (FIG. 2, FIG. 13, FIG. 19, or FIG. 25). The CPU 21 sequentially executes the processing described in each exemplary embodiment of the present invention.

In other words, in such a case, it is conceivable that the present invention can also be made using the blood pressure estimation program. Further, it is conceivable that the present invention can also be made using a computer-readable, non-transitory recording medium storing the blood pressure estimation program.

The present invention has been described using the above-described exemplary embodiments as exemplary cases. However, the present invention is not limited to the above-described exemplary embodiments. In other words, the present invention is applicable with various aspects that can be understood by those skilled in the art without departing from the scope of the present invention.

This application is based upon and claims the benefit of priority from Japanese patent application No. 2014-025372, filed on Feb. 13, 2014, the disclosure of which is incorporated herein in its entirety.

REFERENCE SIGNS LIST

101 Blood pressure estimation device
102 Blood pressure estimation unit
2001 Blood pressure information
2002 Pulse wave information
401 Cuff
402 Pulse wave measurement unit
403 Pulse wave measurement unit
404 Pressure control unit
405 Input unit
406 Display unit
407 Pressure measurement unit
408 Blood pressure measurement device
1101 Blood pressure estimation device
1102 Blood pressure estimation unit
2001 Blood pressure information
2002 Particular pulse wave information
2003 Pressure signal
2004 Pulse wave signal
2005 Pulse wave signal
2006 Blood pressure information
2007 Blood pressure information
1001 Pulse wave measurement unit
1002 Pulse wave measurement unit
1003 Pulse wave measurement unit
1004 Pulse wave measurement unit
1005 Cuff
1006 Pressure bag
1007 Blood pressure measurement device
1008 Blood pressure measurement device
1201 Blood pressure measurement device
1202 Blood pressure estimation device
1203 Pressure control unit
1401 Blood pressure measurement device
1402 Blood pressure estimation device
1403 Pressure control unit
20 Computing device
21 CPU
22 Memory
23 Disk
24 Nonvolatile recording medium
25 Input device
26 Output device
27 Communication IF

The invention claimed is:

1. A blood pressure measurement device comprising:
a blood pressure unit configured to read blood pressure information in which (i) pulse wave information and (ii) a blood pressure for the pulse wave information are associated with each other and estimate a blood pressure for a particular pulse wave information by determining the blood pressure associated with the particular pulse wave information based on the blood pressure information;
a first pulse wave measurement unit configured to measure a pulse wave in a certain time period by using the blood pressure in an upstream of an artery, and transmitting the measured pulse wave to the blood pressure unit as a pulse wave signal; and
a second pulse wave measurement unit configured to measure the pulse wave in the certain time period using the blood pressure in a downstream of the artery and transmitting the measured pulse wave to the blood pressure unit as the pulse wave signal, wherein,
the pulse wave information is information where a pressure signal during the certain time period and the pulse wave signal measured under the pressure signal during the certain time period are associated with each other,
the blood pressure unit calculates a degree of similarity representing an extent that pulse wave information for the pulse wave signal and the particular pulse wave information are similar to each other and estimates, as a particular blood pressure, the blood pressure associated with the pulse wave information in which the degree of similarity is equal to or larger than a particular threshold, and
the blood pressure unit receives the pulse wave signal transmitted by the first pulse wave measurement unit and the pulse wave signal transmitted by the second pulse wave measurement unit and estimates the blood pressure on a basis of the received two pulse wave signals.

2. The blood pressure measurement device according to claim 1, wherein
the pulse wave information represents information where a pulse wave value for the pulse wave signal satisfying a predetermined condition and the blood pressure are associated, and
the degree of similarity represents a degree of similarity between (iii) a pressure value and the pulse wave value associated with each other in the particular pulse wave information and (iv) a pressure value and the pulse wave value associated with each other in the pulse wave information.

3. The blood pressure measurement device according to claim 1, further comprising:
   a signal storage unit configured to store the blood pressure information; and
   a signal search unit configured to read the blood pressure information satisfying a particular condition from the signal storage unit, wherein
   the blood pressure unit estimates a blood pressure for the pulse wave information on a basis of the blood pressure information read by the signal search unit and the particular pulse wave information.

4. The blood pressure measurement device according to claim 1, wherein
   the blood pressure estimation unit estimates the blood pressure in a process of pressurization performed by a cuff.

5. The blood pressure measurement device according to claim 1, wherein
   the first pulse wave measurement unit and the second pulse wave measurement unit are located to sandwich a pressurization center or substantially the center of a shorter side direction in a cuff.

6. The blood pressure measurement device according to claim 1, wherein
   the first pulse wave measurement unit or the second pulse wave measurement unit is a vibration sensor that detects vibrations.

7. A blood pressure measurement method comprising:
   reading, by using an information processing device, blood pressure information in which (i) pulse wave information and (ii) a blood pressure for the pulse wave information are associated with each other and estimating a blood pressure for a particular pulse wave information by determining the blood pressure associated with the particular pulse wave information based on the blood pressure information;
   measuring a pulse wave in a certain time period by using the blood pressure in an upstream of an artery, and first transmitting the measured pulse wave as a pulse wave signal; and
   measuring the pulse wave in the certain time period using the blood pressure in a downstream of the artery and second transmitting the measured pulse wave as the pulse wave signal, wherein,
   the pulse wave information is information where a pressure signal during the certain time period and the pulse wave signal measured under the pressure signal during the certain time period are associated with each other, and
   in the blood pressure, calculating a degree of similarity representing an extent that pulse wave information for the pulse wave signal and the particular pulse wave information are similar to each other and estimating, as a particular blood pressure, the blood pressure associated with the pulse wave information in which the degree of similarity is equal to or larger than a particular threshold, and
   in estimating the blood pressure, receiving the pulse wave signal transmitted in the first transmitting and the pulse wave signal transmitted in the second transmitting and estimating the blood pressure on a basis of the received two pulse wave signals.

8. A non-transitory recording medium recording a blood pressure measurement program that causes a computer to realize
   a blood pressure function configured to read blood pressure information in which (i) pulse wave information and (ii) a blood pressure for the pulse wave information are associated with each other and estimate a blood pressure for a particular pulse wave information by determining the blood pressure associated with the particular pulse wave information based on the blood pressure information;
   a first pulse wave measurement function configured to measure a pulse wave in a certain time period by using the blood pressure in an upstream of an artery, and transmitting the measured pulse wave as a pulse wave signal; and
   a second pulse wave measurement function configured to measure the pulse wave in the certain time period using the blood pressure in a downstream of the artery and transmitting the measured pulse wave to the blood pressure device as the pulse wave signal, wherein,
   the pulse wave information is information where a pressure signal during the certain time period and the pulse wave signal measured under the pressure signal during the certain time period are associated with each other,
   the blood pressure function calculates a degree of similarity representing an extent that pulse wave information for the pulse wave signal and the particular pulse wave information are similar to each other and estimates, as a particular blood pressure, the blood pressure associated with the pulse wave information in which the degree of similarity is equal to or larger than a particular threshold, and
   the blood pressure function receives the pulse wave signal transmitted by the first pulse wave measurement function and the pulse wave signal transmitted by the second pulse wave measurement function and estimates the blood pressure on a basis of the received two pulse wave signals.

* * * * *

UNITED STATES PATENT AND TRADEMARK OFFICE
CERTIFICATE OF CORRECTION

PATENT NO. : 10,194,811 B2  
APPLICATION NO. : 15/118227  
DATED : February 5, 2019  
INVENTOR(S) : Yuji Ohno et al.

Page 1 of 2

It is certified that error appears in the above-identified patent and that said Letters Patent is hereby corrected as shown below:

On the Title Page

Column 2, (57) Abstract, Line 1; After "pressure", insert --estimation--

Column 2, (57) Abstract, Line 2; After "accurate", insert --estimation--

Column 2, (57) Abstract, Line 2, (second occurrence); After "pressure", insert --estimation--

Column 2, (57) Abstract, Line 3; After "pressure", insert --estimation--

In the Specification

Column 22, Description of Embodiment, Line 40; After "1401,", insert --a blood pressure can be estimated with a higher degree of accuracy.--

In the Claims

Column 24, Line 23, (First Occurrence); In Claim 1, after "pressure", insert --estimation--

Column 24, Line 34; In Claim 1, after "pressure", insert --estimation--

Column 24, Line 40; In Claim 1, after "pressure", insert --estimation--

Column 24, Line 45; In Claim 1, after "pressure", insert --estimation--

Column 24, Line 53; In Claim 1, after "pressure", insert --estimation--

Column 25, Line 11, (First Occurrence); In Claim 3, after "pressure", insert --estimation--

Column 26, Line 1; In Claim 7, delete "pressure ," and insert --pressure estimation,-- therefor Signed and Sealed this  
Thirtieth Day of July, 2019

Andrei Iancu  
*Director of the United States Patent and Trademark Office*

CERTIFICATE OF CORRECTION (continued)
U.S. Pat. No. 10,194,811 B2

Column 26, Line 16; In Claim 8, after "pressure", insert --estimation--

Column 26, Line 33; In Claim 8, after "pressure", insert --estimation--

Column 26, Line 38; In Claim 8, after "pressure", insert --estimation--

Column 26, Line 46; In Claim 8, after "pressure", insert --estimation--